United States Patent
Van Laar

(10) Patent No.: US 12,410,481 B2
(45) Date of Patent: Sep. 9, 2025

(54) METHOD OF DIAGNOSIS, STAGING AND MONITORING OF MELANOMA USING MICRORNA GENE EXPRESSION

(71) Applicant: Geneseq Pty. Ltd., Melbourne (AU)

(72) Inventor: Ryan Van Laar, Melbourne (AU)

(73) Assignee: Geneseq Pty. Ltd., Melbourne (AU)

( * ) Notice: Subject to any disclaimer, the term of this patent is extended or adjusted under 35 U.S.C. 154(b) by 0 days.

(21) Appl. No.: 18/451,574

(22) Filed: Aug. 17, 2023

(65) Prior Publication Data
US 2024/0110249 A1 Apr. 4, 2024

Related U.S. Application Data

(62) Division of application No. 16/753,318, filed as application No. PCT/AU2018/051050 on Sep. 26, 2018, now abandoned.

(30) Foreign Application Priority Data

Oct. 3, 2017 (AU) ................................ 2017903978

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2011/0015080 A1* 1/2011 Golub ................ C12N 15/1072
506/13

OTHER PUBLICATIONS

Robert et al. N Eng J Med. 2015. 372: 320-330 (Year: 2015).*
Tumilson et al. (Molecular Neurobiology. 2014. 50: 545-558 (Year: 2014).*
Tian et al PLOS One. Jan. 5, 2012. 7(1): e29551 (Year: 2012).*
Zhou et al Scientific Reports. Jun. 10, 2015. 6:11251 (Year: 2015).*
Heggard et al International Journal of Cancer. May 4, 2011. 102. 130: 1378-1386 (Year: 2011).*
Fogli et al. Tumor Biology. May 2017.39: 1-8 (Year: 2017).*
Babapoor et al. Laboratory Investigation. Feb. 2017. 97: 636-648 (Year: 2017).*
Kwok et al Hum. Vaccin & Immunotherapeutics. 12(1): 2777-2789; see abstract and p. 1778, col. 2 (Year: 2016).*
Zhou et al Frontiers in Pharmacology. 2019. 10: 387, 12 pages (Year: 2019).*

* cited by examiner

*Primary Examiner* — Carla J Myers
(74) *Attorney, Agent, or Firm* — Hodgson Russ LLP

(57) ABSTRACT

The present invention relates to methods of diagnosing melanoma in a subject, the method comprising detecting microRNA expression levels. The present invention also relates to methods of assessing the disease stage of melanoma and/or monitoring said melanoma stage. Also, the present invention relates to selecting a treatment or modifying a treatment based on the diagnosis or stage of melanoma. Further the present invention relates to a system for detecting and diagnosing melanoma in a patient and for determining the disease stage of melanoma.

6 Claims, 12 Drawing Sheets

Figure 1:
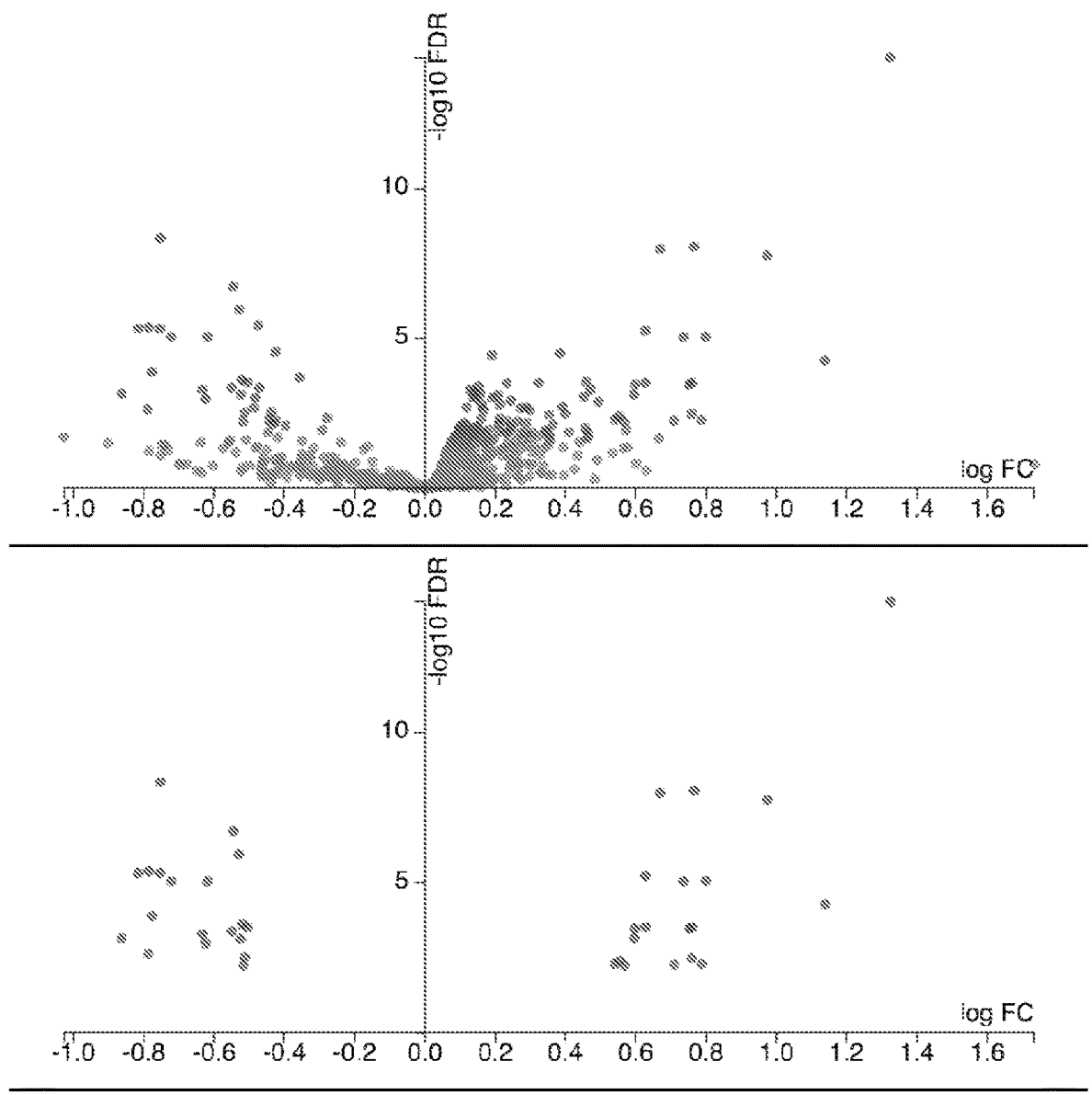

Specification includes a Sequence Listing.

METHOD OF DIAGNOSIS, STAGING AND MONITORING OF MELANOMA USING MICRORNA GENE EXPRESSION

CROSS-REFERENCE TO RELATED APPLICATIONS

This application is a divisional of U.S. patent application Ser. No. 16/753,318, filed on Apr. 2, 2020, which is a National Stage application of International Application No. PCT/AU2018/051050, filed on Sep. 26, 2018, which claims priority to Australian patent application No. 2017903978, filed on Oct. 3, 2017, all the disclosures of which are incorporated herein by reference in their entirety.

SEQUENCE LISTING

The instant application contains a Sequence Listing, which has been submitted electronically in .xml format and is hereby incorporated by reference in its entirety. The .xml copy, created Aug. 16, 2023, is named "011417_00031_ST26.xml" and is 43,076 bytes in size.

FIELD OF THE INVENTION

The present invention relates to methods of diagnosing melanoma in a subject, the method comprising detecting microRNA expression levels. The present invention also relates to methods of assessing the disease stage of melanoma and/or monitoring said melanoma stage. Also, the present invention relates to selecting a treatment or modifying a treatment based on the diagnosis or stage of melanoma. Further the present invention relates to a system for detecting and diagnosing melanoma in a patient and for determining the disease stage of melanoma.

BACKGROUND OF THE INVENTION

Globally, over 130,000 individuals are diagnosed with melanoma each year. Whilst melanoma is the least common form of skin cancer, it is also the deadliest. Incidence rates have increased over the past 10 years as atmospheric ozone levels are depleted and solar UV radiation increases proportionally. Risk factors for developing melanoma include fair skin, freckling, and light hair; recreational and occupational sun exposure; a family or previous personal history of skin cancer; having a weakened immune system; being older or being male.

Residents of Australia have the highest incidence of melanoma in the world, with one in 14 males and one in 23 females expected to develop melanomas in their lifetime. These rates are 3-times higher than the USA and 4-times of the UK and have increased by 16% in males and 24% in females over the last decade. In Australia alone, one person every six hours will die from melanoma, an annual death toll that exceeds the national road toll. Over 14,000 Australians are expected to be diagnosed with melanoma in 2018. Melanoma represents only 2% of all skin cancers, yet causes 75% of skin cancer deaths.

Diagnosed early in its progression, melanoma has extremely high survival rates. Identified and removed at stage 1, 95% of patients are alive 10 years after diagnosis. When diagnosed at stage IV, the 10-year survival rate drops to 10-15%, underscoring the need for early detection and the potential clinical uptake of an accurate, non-invasive diagnostic assay.

In some countries, up to 50% of the population receives whole-body imaging, however this has yet to show a significant impact on mortality rates. There are no widely available, evidence-based methods for routine screening of melanoma.

Therefore there is an urgent unmet need for an objective method for detecting the presence of active, malignant melanoma cells using non-invasive, low cost, high throughput methods. Further, there is a requirement to not only diagnose melanoma in its early and most treatable stages, but identify staging/prognosis information which may inform treatment options. An accurate non-invasive, such as a blood based or urine based biomarker of melanoma would also be useful in the post-treatment setting, where methods for monitoring long-term treatment response and predicting recurrence are needed.

SUMMARY OF THE INVENTION

The present inventor(s) have identified microRNA biomarker signatures which are useful in the diagnosis, staging and monitoring of melanoma in a subject.

In one embodiment, the invention provides a method for detecting and diagnosing melanoma in a subject, comprising:
(i) detecting microRNA expression levels in a biological sample,
(ii) calculating a classification score (CS) of the biological sample based on one or more algorithms derived from a dataset comprising the expression levels of said microRNAs, and
(iii) classifying the biological sample as melanoma or not based on the value of the classification score wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p, hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In an embodiment, the method for detecting and diagnosing a melanoma in a subject, wherein the microRNA consist of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In a related aspect the method for detecting and diagnosing a melanoma in a subject the microRNA consist of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764

In a further related aspect the method for detecting and diagnosing a melanoma in a subject the microRNA consist of:

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p.

The biological sample is solid tissue, plasma, blood, skin, exosomes, urine, milk, serum, ascites, cyst fluid, pleural fluid, peritoneal fluid, cerebral spinal fluid, tears, saliva, sputum, hair or combinations thereof.

In an embodiment, the subject is a human.

The present invention also provides a method of determining the disease stage of melanoma said method comprising
  (i) detecting microRNA expression levels in a biological sample,
  (ii) calculating a staging score (SS) of the biological sample based on a dataset comprising the expression levels of said microRNAs, and
  (iii) classifying the biological sample as a stage of melanoma based on the value of the staging score
wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In a related aspect the method of determining the disease stage of melanoma the microRNA consist of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In another related aspect the method of determining the disease stage of melanoma the microRNA consist of: hsa-let-7e-5p, hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p
hsa-miR-331-3p,
hsa-miR-337-5p,
hsa-miR-4787-3p,
hsa-miR-521,
hsa-miR-652-3p,
hsa-miR-660-5p In an embodiment the staging of the melanoma is stage I or II or III or IV.

The biological sample is solid tissue, plasma, blood, skin, exosomes, urine, milk, serum, ascites, cyst fluid, pleural fluid, peritoneal fluid, cerebral spinal fluid, tears, saliva, sputum, hair or combinations thereof.

In an embodiment, the subject is a human.

In an embodiment, the invention provides a method for monitoring melanoma in a subject, wherein the level of expression of at least one microRNA is selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p, -continued hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

The invention provides a method for monitoring melanoma in a subject, wherein the microRNA consist of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p, hsa-miR-548ad-3p,
hsa-miR-548l,
hsa-miR-553,
hsa-miR-624-3p,
hsa-miR-652-3p,
hsa-miR-660-5p,
hsa-miR-764

The invention provides a method for monitoring melanoma in a subject, wherein the microRNA consist of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764

The invention provides a method for monitoring melanoma in a subject, wherein the microRNA consist of:

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p.

The biological sample is solid tissue, plasma, blood, skin, exosomes, urine, milk, serum, ascites, cyst fluid, pleural fluid, peritoneal fluid, cerebral spinal fluid, tears, saliva, sputum, hair or combinations thereof.

In an embodiment, the subject is a human.

The present invention provides a method of monitoring the status of melanoma for relapse or recurrence in a subject previously diagnosed with melanoma, said method comprising
(i) detecting microRNA expression levels in a biological sample,
(ii) calculating a classification score (CS) of the biological sample based on one or more algorithms from a dataset comprising the expression levels of said microRNAs, and
(iii) classifying the biological melanoma or not based on the value of the classification score and comparing to a previously determined classification threshold, which separates those with melanoma from those without
wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In an embodiment, said microRNA consist of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In a further embodiment, said microRNA consist of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p, hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764

In yet another embodiment, said microRNA consist of:

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p The present invention also provides a method for treating melanoma in a subject comprising administering to said subject a therapeutically effective amount of an agent wherein said agent modifies directly or indirectly the expression level of at least one miRNA, wherein said at least one miRNA is selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In an aspect, the present invention provides a method for treating melanoma in a subject comprising administering to said subject a therapeutically effective amount of an agent wherein said agent modifies directly or indirectly the expression level of miRNA consisting of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In a further aspect, the present invention provides a method for treating melanoma in a subject comprising administering to said subject a therapeutically effective amount of an agent wherein said agent modifies directly or indirectly the expression level of miRNA consisting of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764

In a further aspect, the present invention provides a method for treating melanoma in a subject comprising administering to said subject a therapeutically effective amount of an agent wherein said agent modifies directly or indirectly the expression level of miRNA consisting of:

hsa-let-7e-5p,
hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p In yet a further aspect, the present invention provides a method for treating melanoma in a subject comprising administering to said subject a therapeutically effective amount of an agent wherein said agent modifies directly or indirectly the expression level of miRNA consisting of:

hsa-miR-1258,
hsa-miR-1264,
hsa-miR-1302,
hsa-miR-152-3p,

-continued hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p The biological sample is solid tissue, plasma, blood, skin, exosomes, urine, milk, serum, ascites, cyst fluid, pleural fluid, peritoneal fluid, cerebral spinal fluid, tears, saliva, sputum, hair or combinations thereof.

In an embodiment, the subject is a human.

In a further aspect, the present invention comprises selecting a treatment or modifying a treatment following an adverse melanoma outcome based on the expression levels of at least one microRNA determined by the classification score, said method comprising administering an agent effective in the treatment of melanoma which modifies directly or indirectly the expression level of at least one miRNA in said subject wherein said at least one or more miRNA is selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p, -continued hsa-miR-652-3p,
hsa-miR-660-5p,
hsa-miR-764;

In an aspect, the present invention comprises selecting a treatment or modifying a treatment following an adverse melanoma outcome based on the expression levels of microRNA determined by the classification score, said method comprising administering an agent effective in the treatment of melanoma which modifies directly or indirectly the expression level of miRNA consisting of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;
or
(b)

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764
or
(c)

hsa-let-7e-5p,
hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p
or
(d)

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p The biological sample is solid tissue, plasma, blood, skin, exosomes, urine, milk, serum, ascites, cyst fluid, pleural fluid, peritoneal fluid, cerebral spinal fluid, tears, saliva, sputum, hair or combinations thereof.

In an embodiment, the subject is a human.

In another aspect, the present invention provides use of an agent which modifies the expression level of at least one miRNA for the production of a medicament effective in the treatment of melanoma wherein said at least one microRNA is selected from the following:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;

In one aspect, the present invention provides use of an agent which modifies the expression level of miRNA for the production of a medicament effective in the treatment of melanoma wherein said microRNA consists of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;
or
(b)

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764
or
(c)

hsa-let-7e-5p,
hsa-miR-105-5p,
hsa-miR-1180-3p,
hsa-miR-127-5p,
hsa-miR-152-3p,

-continued hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p
or
(d)

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p In an embodiment, the agent is selected from one or more of the following:
  (i) Immunotherapy, including: Aldesleukin (IL-2), Intron A (Recombinant Interferon Alfa-2b), Ipilimumab, Keytruda (Pembrolizumab), Pembrolizumab, Sylatron (Peginterferon Alfa-2b), Yervoy (Ipilimumab), Zelboraf (Vemurafenib),
  (ii) Targeted/small-molecule therapy, including: Cobimetinib, Dabrafenib, Mekinist (Trametinib), Nivolumab (Opdivo), Vemurafenib
  (iii) Chemotherapy, including: Dacarbazine
  (iv) Viral therapy, including: Imlygic (Talimogene Laherparepvec)
  (v) siRNA
  (vi) antisense nucleic acids,
  (vii) antagonist microRNAs: including, antagomirs,
  (viii) enzymatic RNA molecules: including, ribozymes
  (ix) miRNA agonist; and/or
  (x) anti-miRNA antibodies In another aspect, there is provided a system for detecting and diagnosing melanoma in a patient,
  at least one processor; and
  at least one storage medium containing program instructions for execution by said processor, said program instructions causing said processor to execute steps comprising:
  (i) detecting microRNA expression levels in a biological sample from the patient,
  (ii) calculating a classification score (CS) of the biological sample based on one or more algorithms derived from a dataset comprising the expression levels of said microRNAs, and
  (iii) classifying the biological sample as melanoma or not based on the value of the classification score;
wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764.

In a further aspect, the microRNA consists of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.

hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;
or
(b)

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764
or
(c)

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.

hsa-miR-4532,
hsa-miR-454-3p,
hsa-miR-497-5p,
hsa-miR-548a-5p,
hsa-miR-548ad-3p

One or more algorithms may comprise a trained support vector machine (SVM) algorithm trained using samples from the dataset, the SVM is configured to classify the biological sample as belonging to a class corresponding to melanoma if an inner sum of weights and expression of the microRNA is greater than a predetermined threshold.

One or more algorithms may comprise a nearest-centroid classifier, the nearest-centroid classifier is configured to assign a melanoma class to the biological sample if the centroid of the microRNA of the biological sample is closer to a melanoma centroid of the microRNA instead of a normal centroid of the microRNA.

One or more algorithms may comprise a compound covariate predictor, the compound covariate predictor is configured to classify the biological sample as belonging to a class corresponding to melanoma if an inner sum of weights and expression of the microRNA is greater than a predetermined threshold is configured to classify the biological sample as belonging to a class corresponding to melanoma if an inner sum of weights and expression of the microRNA is greater than a predetermined threshold.

In another aspect, there is provided a system for determining the disease stage of melanoma, said system comprising:
at least one processor; and
at least one storage medium containing program instructions for execution by said processor, said program instructions causing said processor to execute steps comprising:
(i) detecting microRNA expression levels in a biological sample,
(ii) calculating a staging score (SS) of the biological sample based on a dataset comprising the expression levels of said microRNAs, and
(iii) classifying the biological sample as a stage of melanoma based on the value of the staging score
wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p, hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In another aspect, the microRNA consist of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764 or (b)

hsa-let-7e-5p,
hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p The staging score may be calculated by any algorithm from the group consisting of: logistic regression model, multi-class algorithm comprising four staging classes, nearest centroid classifier, support vector machine and binary decision tree classifier.

In a further aspect, the present invention provides a molecular array or a series of reagents, comprising a plurality of:
(i) nucleic acid molecules comprising a nucleotide sequence corresponding to any one or more of the microRNA listed in Table 1 or a sequence exhibiting at least 80% identity thereto or a functional derivative, fragment, variant or homologue of said nucleic acid molecule; or
(ii) nucleic acid molecules comprising a nucleotide sequence capable of binding to any one or more of the sequences of (i) under medium stringency conditions or a functional derivative, fragment, variant or homologue of said nucleic acid molecule; or
(iii) nucleic acid probes or oligonucleotides comprising a nucleotide sequence capable of hybridising to any one or more of the sequences of (i) under medium stringency conditions or a functional derivative, fragment, variant or homologue of said nucleic acid molecule;
wherein the level of expression of said microRNA of (i)-(iii) is used to calculate a classification score (CS) which is indicative of the presence or absence of melanoma in a subject or a staging score (SS) which is indicative of the stage of melanoma in a subject.

In a further embodiment, the microRNA of (i)-(iii) used to calculate a classification score (CS) are selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p, -continued hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;

In an embodiment, the microRNA of (i)-(iii) used to calculate a classification score (CS) consist of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p, hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;
or
(b)

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764
or
(c)

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p In another embodiment, the microRNA of (i)-(iii) used to calculate the staging score (SS) consist of:

hsa-let-7e-5p,
hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p In another aspect, the present invention provides a diagnostic kit for the diagnosis of a melanoma, assessment of disease stage or assessment of disease susceptibility of melanoma to a proposed treatment comprising:
 a. at least one "forward" amplification primer; and/or
 b. at least one "reverse" amplification primer; and/or
 c. detection or capture probes for the microRNA
wherein the primers enable specific amplification of the nucleotide sequences of at least one microRNA selected from Table 1.

In a further embodiment, the microRNA consist of:

(a)

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764;
or
(b)

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764
or
(c)

hsa-let-7e-5p,
hsa-miR-105-5p,
hsa-miR-1180-3p,
hsa-miR-127-5p,
hsa-miR-152-3p,
hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-5p
or
(d)

hsa-miR-1258,
hsa-miR-1264,
hsa-miR-1302,
hsa-miR-152-3p,
hsa-miR-154-5p, hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p In an embodiment, the subject is a human.

Any embodiment herein shall be taken to apply mutatis mutandis to any other embodiment unless specifically stated otherwise. For instance, as the skilled person would understand examples of biomarker signatures outlined above for methods of the invention equally apply to the uses of the invention. The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1: Upper panel: all 800 microRNAs evaluated for differential expression between plasma from melanoma patients and normal controls. Lower panel: 38-gene selection based on exclusion of genes not expressed over baseline and statistically significant difference (FDR<0.01 and FC>2) between classes. Genes in the top right and top left of each panel are the most biologically (fold-change) and statistically (FDR) significant differentiators of melanoma from normal controls.

Figure 2:
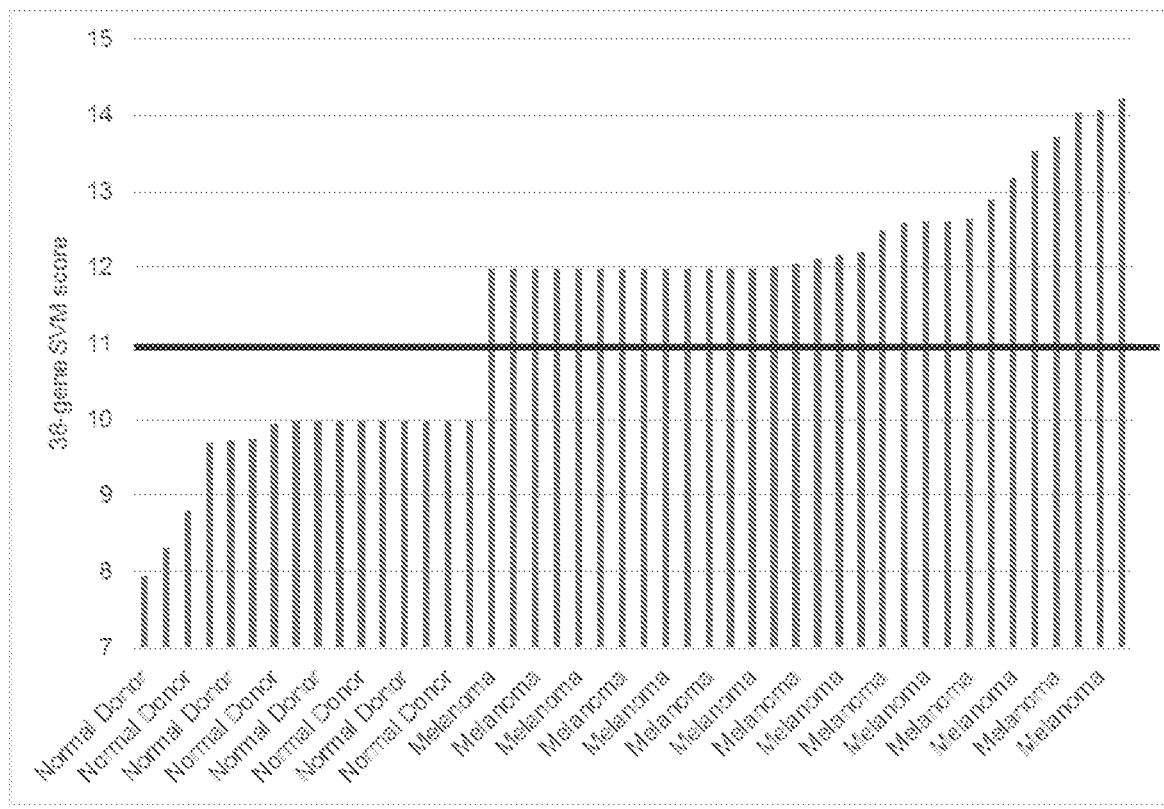

FIG. 2 shows 38-gene SVM scores for samples in the MEL38 discovery database. In this analysis, SVM scores >11 correspond to a melanoma result.

Figure 3:
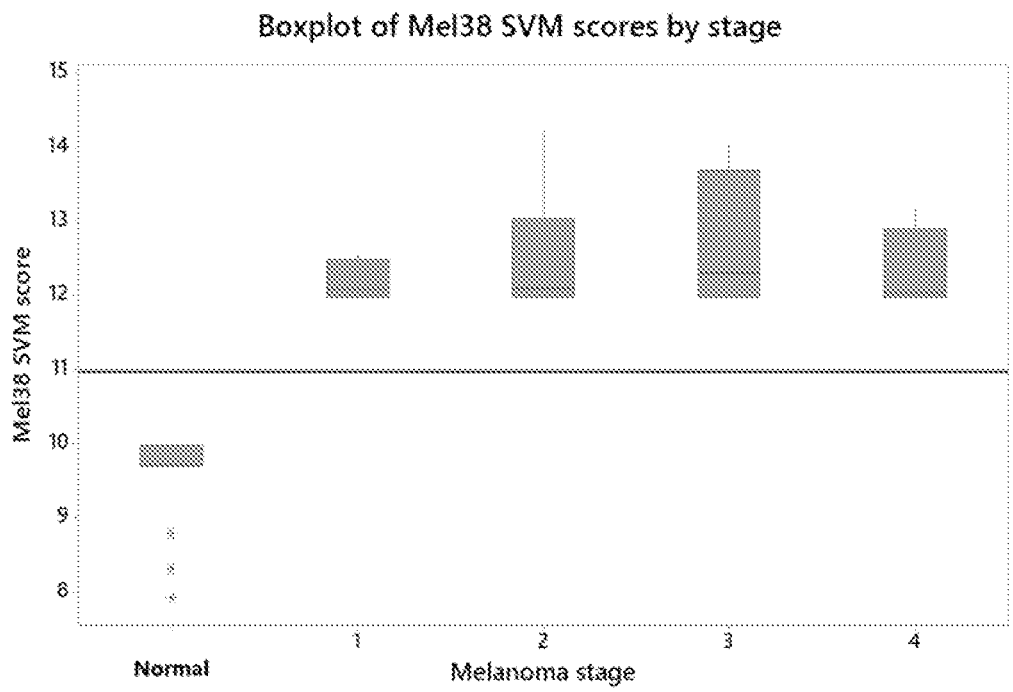

FIG. 3: Box plot analysis of SVM scores generated for each sample in the discovery database, grouped by melanoma stage.

Figure 4:
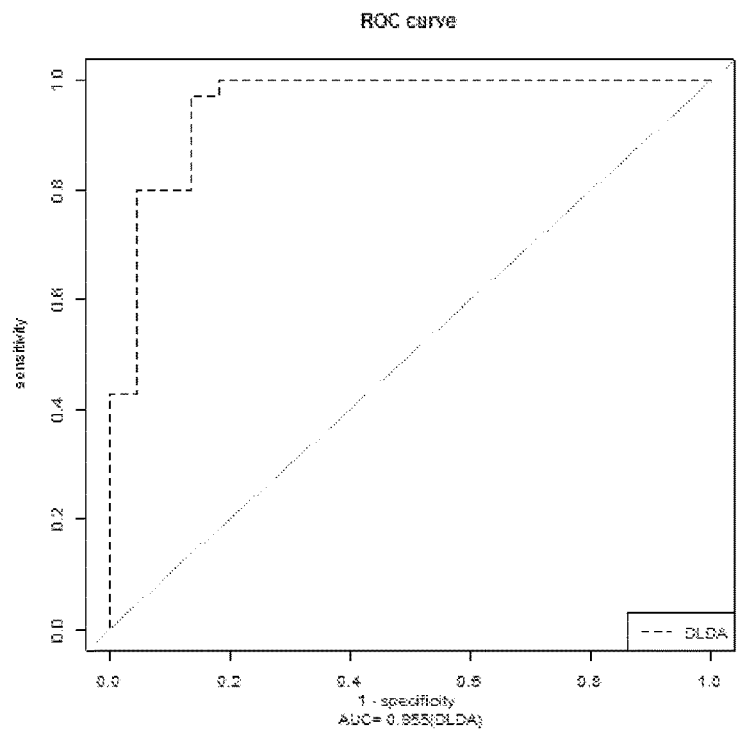

FIG. 4: Area under the curve analysis for 28/32-gene SVM analysis of the independent validation. Partial re-training of the SVM performed AUC=0.96

Figure 5:
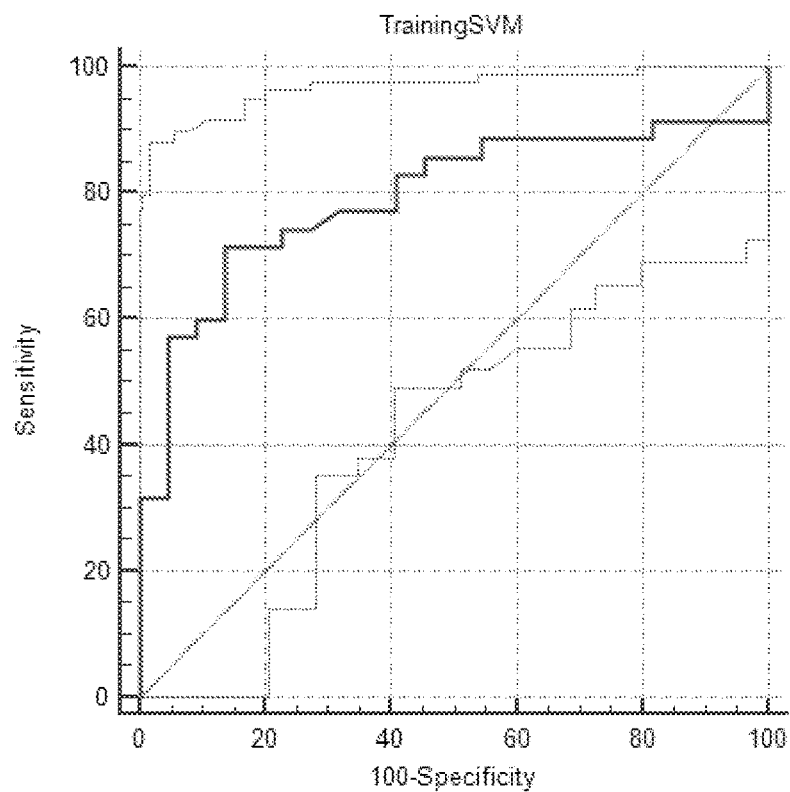

FIG. 5: Area under the curve analysis for 28/32-gene SVM analysis of the independent validation, without additional retraining. AUC=0.798

Figure 6:
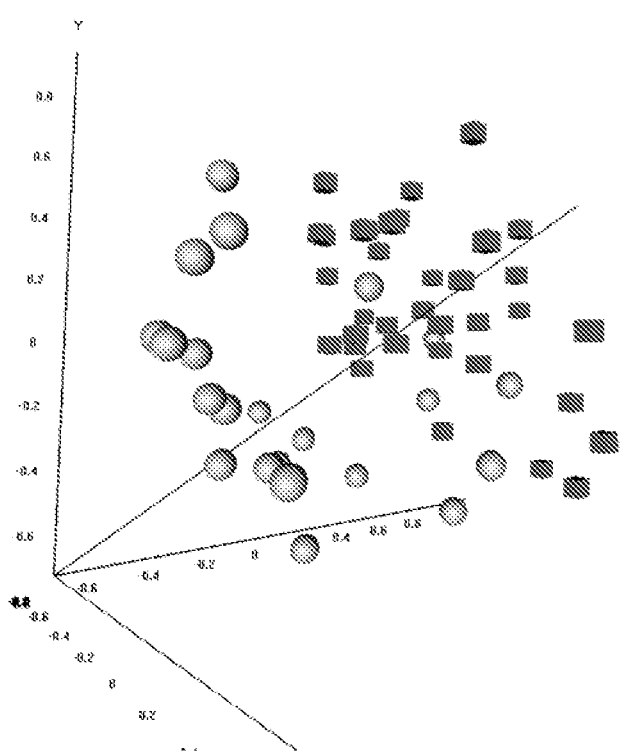

FIG. 6: Multi-dimensional scaling of plasma and normal control microRNA gene expression profiles using 28/38 genes identified from sphere=normal, cube=melanoma FIG. 7: Cross validation of PAM classification models using subsets of the MEL38 gene signature on the discovery (upper panel) and independent validation (lower) databases.

Figure 8:
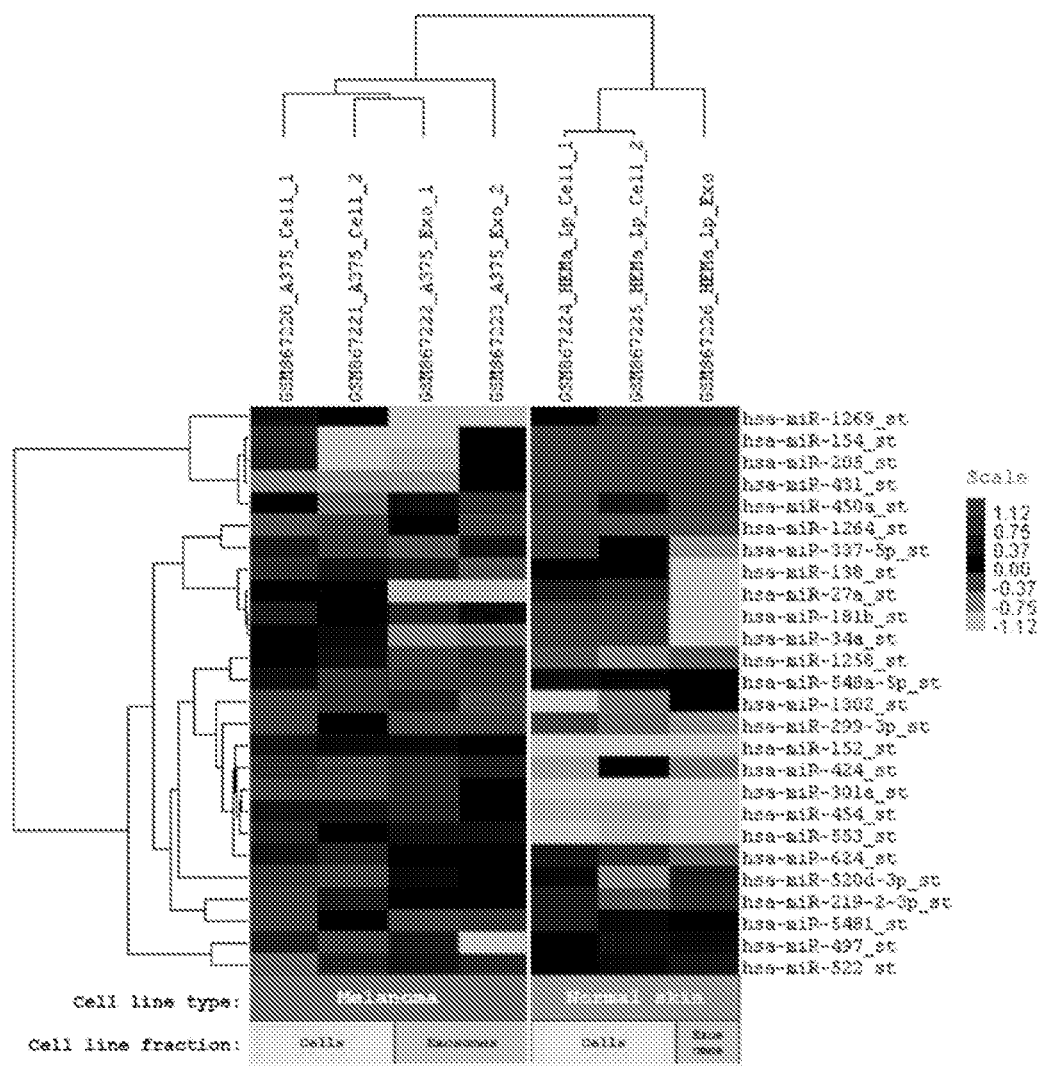

FIG. 8: Hierarchical clustering of microRNA expression levels (Affymetrix MicroRNA GeneChip) in melanoma cells, normal melanocytes and exosomes isolated from the tissue culture media of each cell line.

Figure 9:
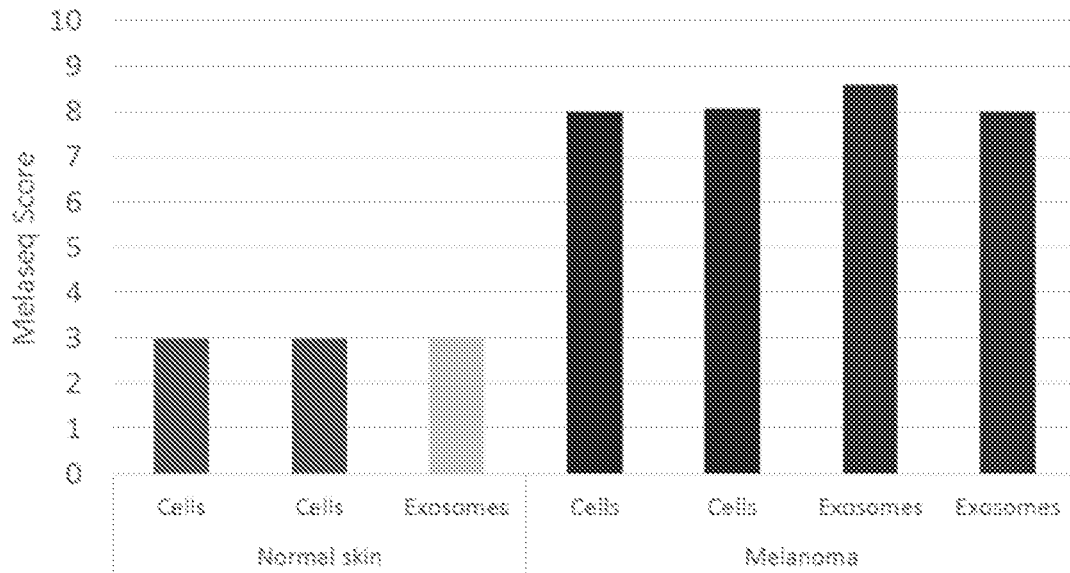

FIG. 9: SVM-classification scores calculated for the melanoma cell, melanoma exosome, normal melanocyte cell and exosome profiles using the matched MEL38 gene signature.

Figure 10:
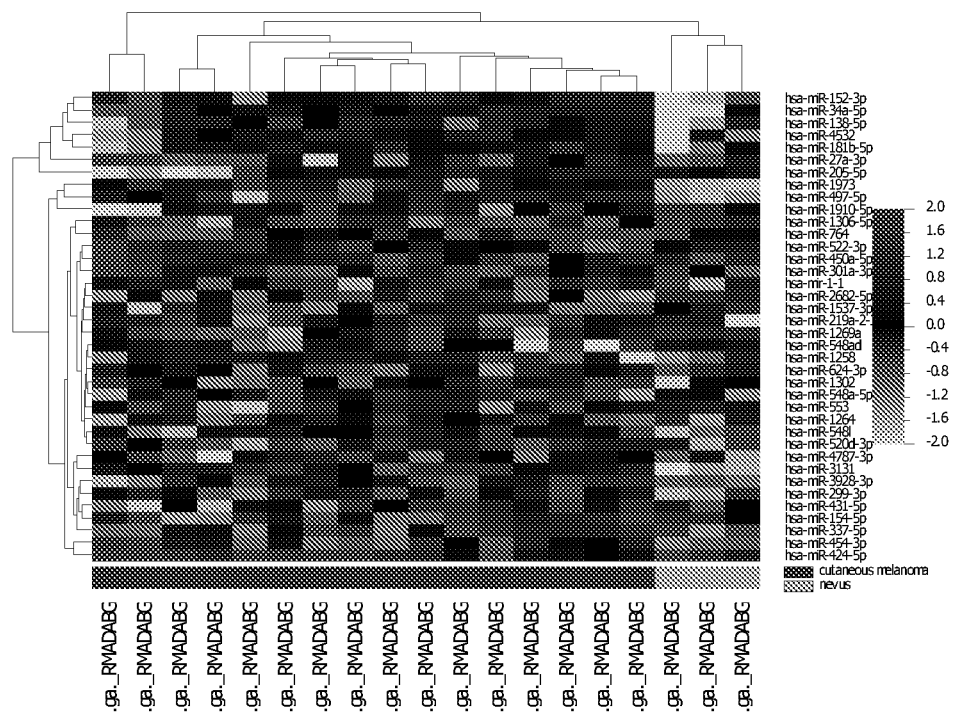

FIG. 10: Hierarchical clustering of MEL38 measured in melanoma and nevus (benign) tissue samples (FFPE).

Figure 11:
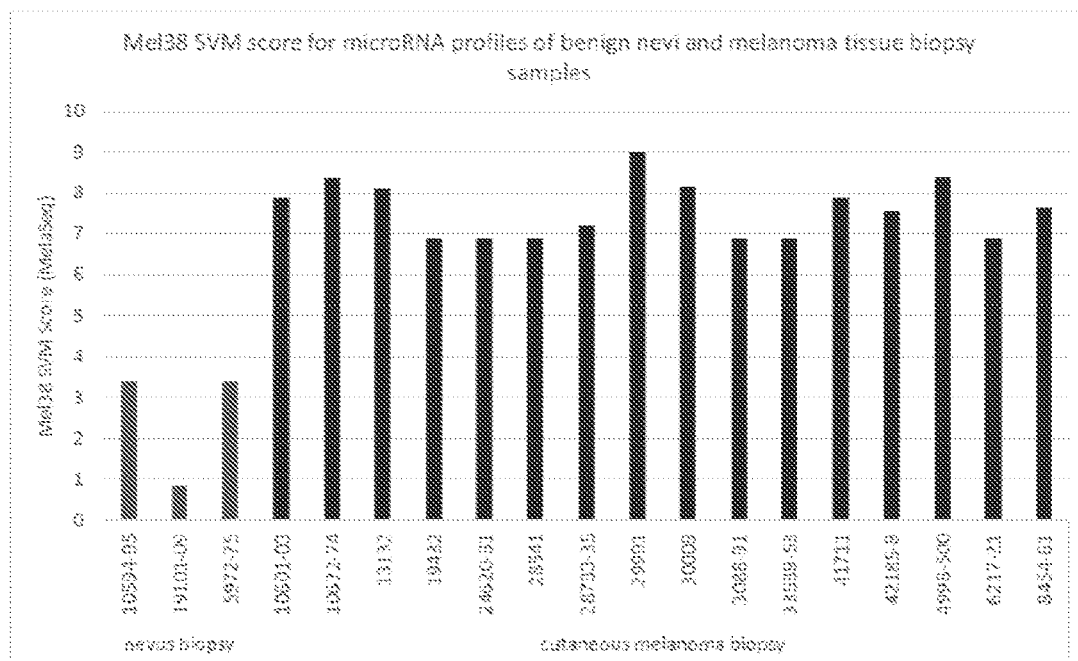

FIG. 11: MEL38 SVM scores calculated for each melanoma and nevus tissue biopsy sample.

Figure 12:
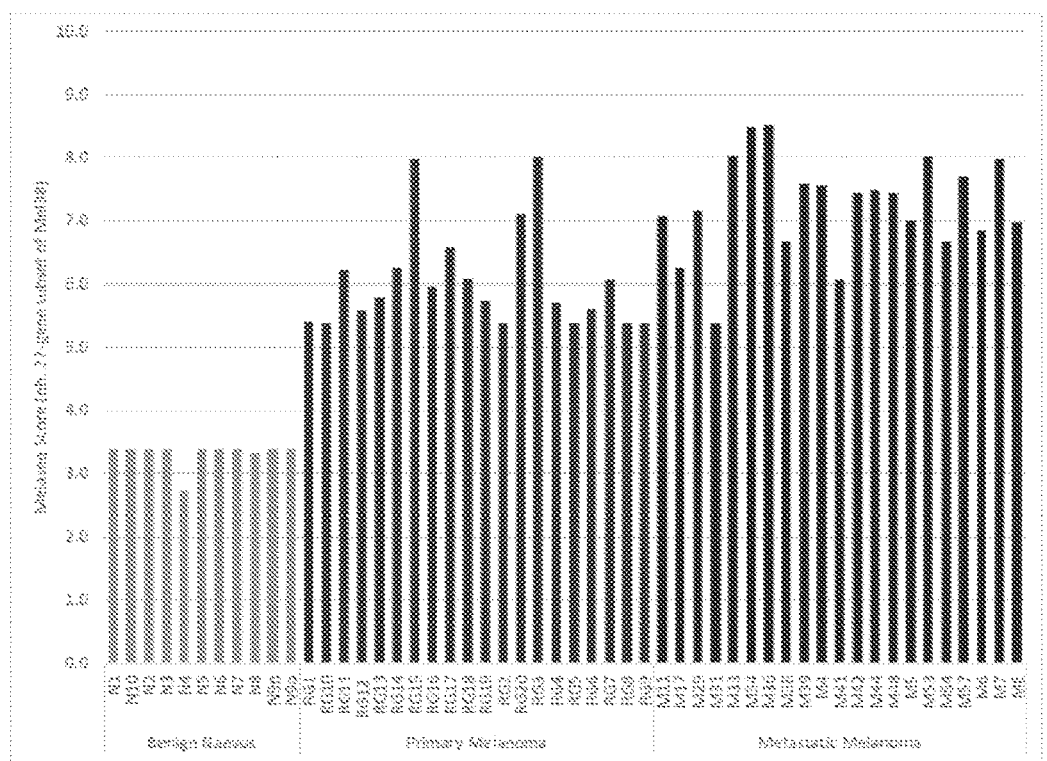

FIG. 12: Classification scores of naevi vs melanoma FFPE samples using a 27-microRNA subset of MEL38

Figure 13:
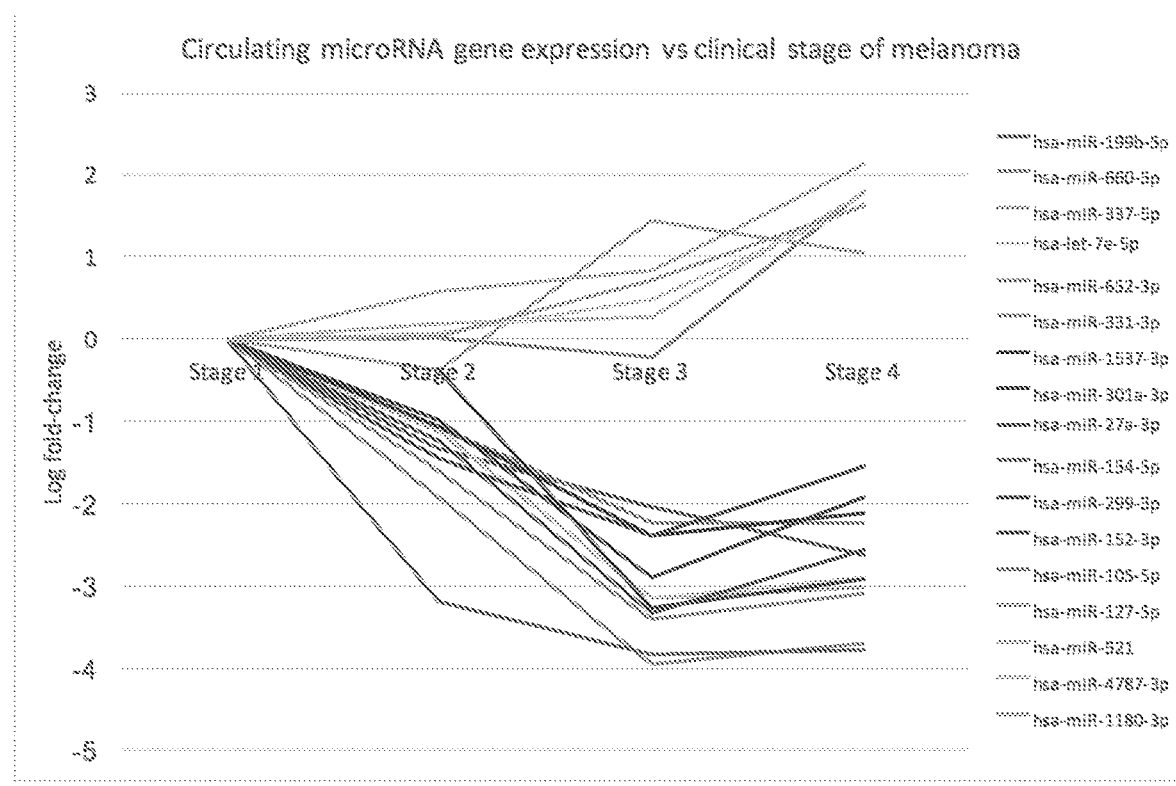

FIG. 13: Mean fold-change expression levels of the 18-gene melanoma-stage signature identified in the plasma of patients stage I-IV disease. Changes are shown as relative to their expression in patients with Stage I disease.

Figure 14:
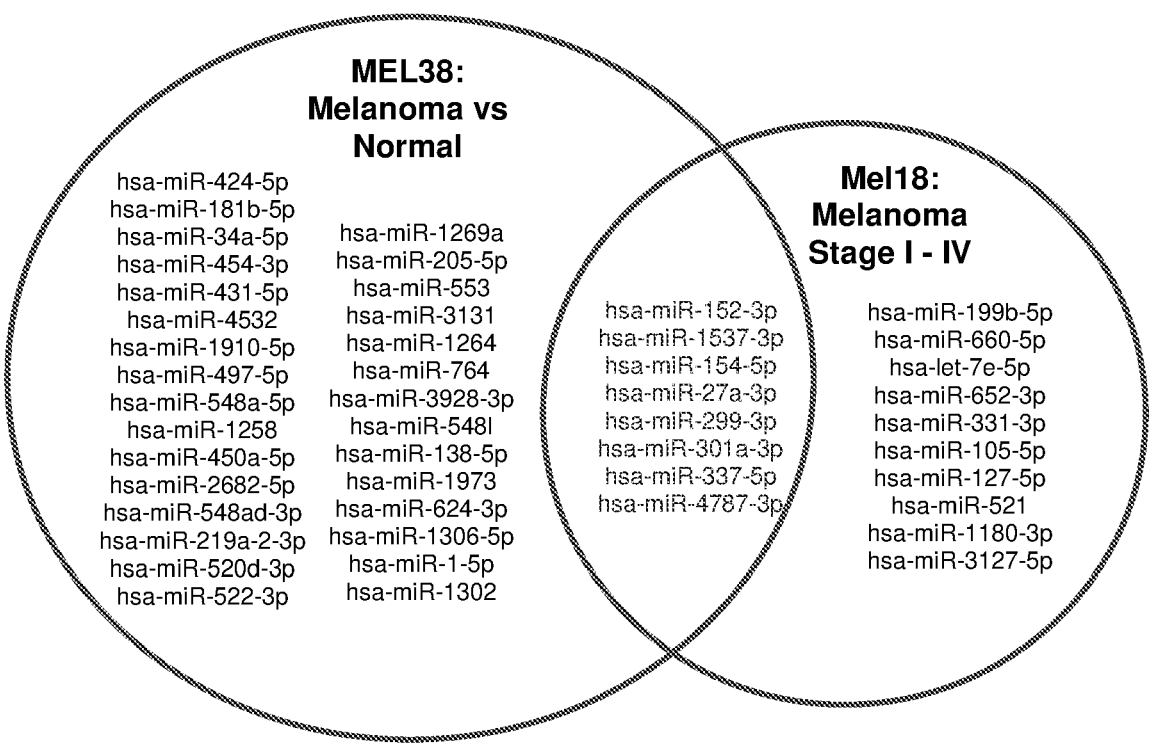

FIG. 14: Venn diagram of microRNAs in the MEL38 diagnostic gene signature and the MEL18 staging gene signature. Total n=48, overlap=8.

Figure 15:
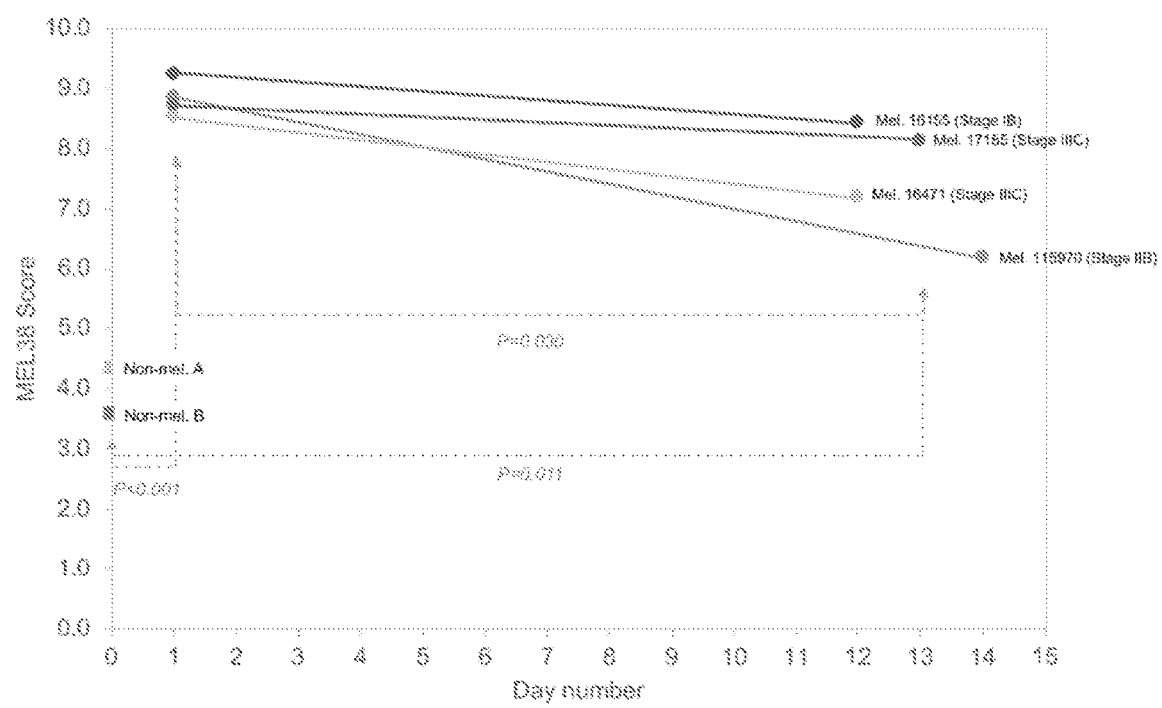

FIG. 15: MEL38 scores in non-melanoma normal control plasma samples and melanoma patient plasma collected before and after surgical excision.

Figure 16:
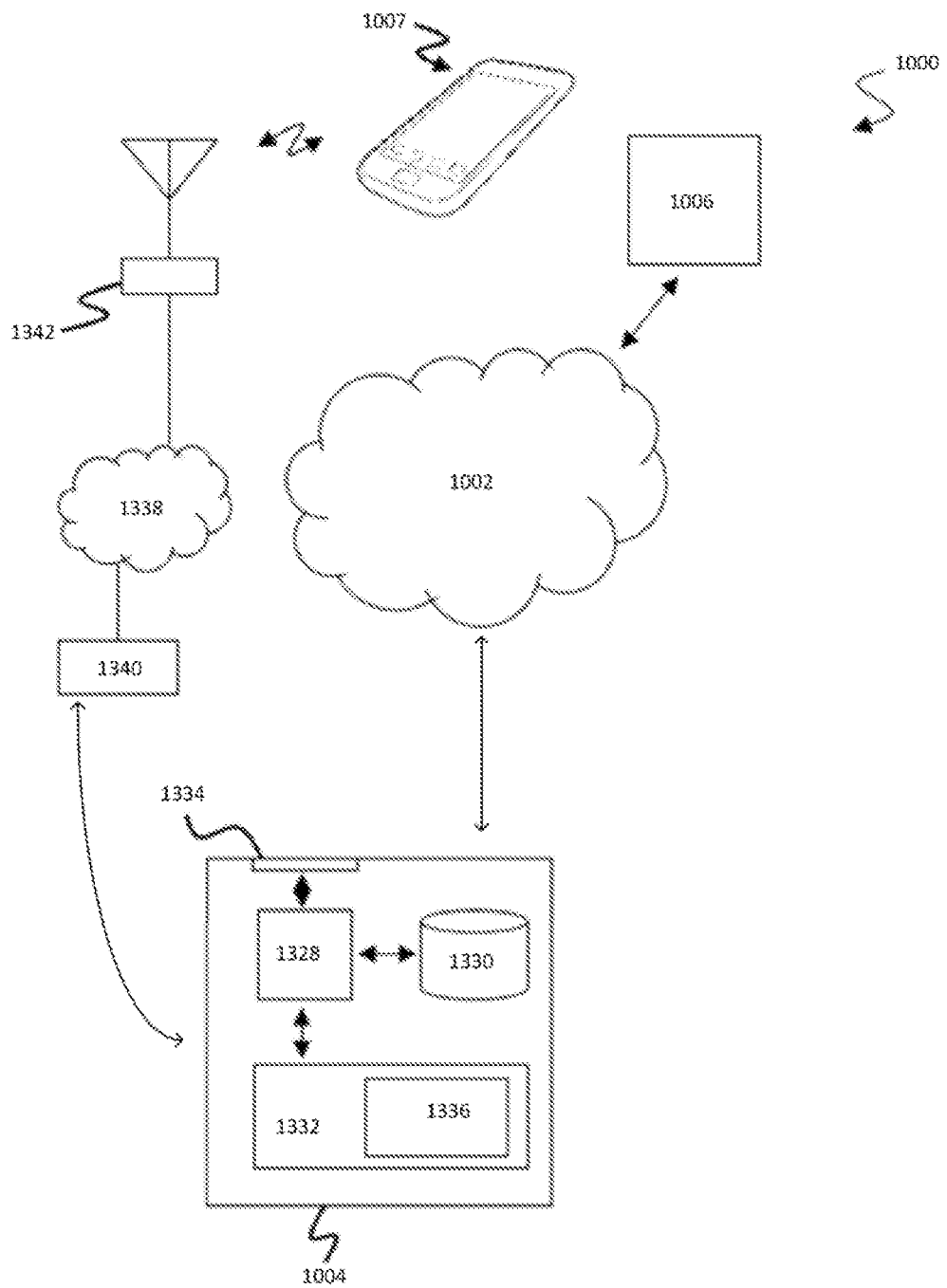

FIG. 16: Block diagram illustrating an exemplary system architecture embodying the invention.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., molecular biology, cell culture, immunology, immunohistochemistry, protein chemistry, and biochemistry).

Unless otherwise indicated, the techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Homes (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning. Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Melanoma

Melanoma originates from uncontrolled proliferation of specialized melanocytes normally responsible for producing pigments in the epithelial layer. Though typically associated with the skin, these cells can also be present in the eye, bone and heart, and cancer lesions can develop in any of these locations. Staging of the melanoma at the time of diagnosis incorporates thickness, mitotic index, ulceration, and sentinel lymph node status, and is generally indicative of clinical outcome. Melanoma is curable for most patients whose primary tumors are adequately removed; however, many patients suffer recurrence and progress to advanced disease and death. The vast majority of recurrent patients present with metastatic disease, from which they eventually succumb.

Melanoma may be classified into the following categories:
1. Superficial spreading melanoma: This is the most common type of melanoma making up about 50% of all melanomas diagnosed. This melanoma usually appears as a dark spot with irregular borders that spreads across the skin.
2. Nodular melanoma: Nodular is one of the most rapidly growing types of melanoma. It appears as a raised lump or 'nodule' and can be brown, black, pink or red in colouring, or have no colour at all. About 15% of all melanomas are nodular.
3. Lentigo maligna melanoma: Lentigo maligna melanomas begin as large freckles. They are commonly found in older people, often in areas that have received a lot of sun exposure such as the face, head, neck and upper body. This type of melanoma makes up 10% of all melanomas.
4. Acral lentiginous melanoma: Acral is a rare type of melanoma that tends to grow on the palms of hands, soles of the feet or under the nails (subungual). It accounts for about 3% of all melanomas.
5. Other, less common types of melanoma include desmoplastic and naevoid melanoma. Mucosal melanomas can be found in tissues in the respiratory, digestive, and reproductive tracts. Uveal (ocular) melanomas develop in the eye.

MicroRNA

The terms "miR", "miRNA" and "microRNA" are used synonymously and refer to a class of about 17-25 nucleotides (nt) long non-coding RNAs derived from endogenous genes.

There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 18 to about 25 nt in length.

MicroRNAs function by engaging in base pairing (perfect or imperfect) with specific sequences in their target genes' messages (mRNA). If the microRNAs match 100% to their target, i.e. the complementarity is complete, the target mRNA is cleaved, and the miRNA acts like a siRNA. If the match is incomplete, i.e. the complementarity is partial, then the translation of the target mRNA is blocked.

The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance towards gaining apoptosis signaling.

It is thought that expression levels of roughly a third of human genes are regulated by miRNAs, and that the miRNA regulation of unique gene expressions is linked to the particular signaling pathway for each specific cell type. For example, the apoptosis signaling pathway may be dictated by a group of miRNAs targeted to destabilize pro-survival gene messages, allowing alternative pro-apoptosis genes to gain dominance and thus activate the death program. Another example is the control of cancer growth; a recent discovery has shown that miRNAs may also be essential in preventing cells from becoming neoplastic. For example, two oncogenes, cMyc and cRas, are found to share control by one miRNA species, whose expression is down-regulated in cancer. In other words, lack of this miRNA allows the unchecked expression of cMyc and cRas, thus permitting these two genes to become abundantly present in cancer cells, allowing them to acquire uncontrolled cell proliferating ability, and set the stage for neoplastic growth.

It is possible that a coordinated orchestration of multiple pathways serves to control a particular cellular state, wherein certain molecular "hubs" may be involved, which are functionally manipulated by hierarchical orders and redundancy of molecular control. Indeed, dozens of miRNAs may operate to ensure that these "hubs" can exert either major or minor functions in cells, by simply repressing the expression of either themselves or their functional opponents. Thus, one gene product may function as a major "hub" for one signaling pathway in one type of cell, and in another cell type, it may be a minor "hub", or may not be used at all. MicroRNA control of "hub" gene expressions may then be an expedient mechanism to provide such versatility for various molecules to serve as either major or minor "hubs", or not at all, for different types of cellular operational modalities.

Given the role of miRNAs in gene regulation, and in many physiological and pathological processes, information about their interactive modes and their expression patterns is desirable to obtain. Systems and methods of quantitating and identifying which groups of putative miRNAs are in operation in a particular cell type, or in association with a particular process or condition of interest, can provide information useful for understanding how each cellular state evolves and is maintained, and how dysfunctional maintenance is abetted by improper decreases or increases of unique sets of miRNAs to regulate the expression of key genes. Such understanding can prove useful in the diagnosis and characterization of a number of disorders, including cancer.

The level of miRNAs in blood and other body fluids such milk, blood, serum, plasma, ascites, cyst fluid, pleural fluid, peritoneal fluid, cerebral spinal fluid, tears, urine, saliva, sputum are known to change in response to altered disease state, physiological mechanisms and tissue injury. It has been demonstrated that tumour cells release miRNAs into the circulation and that blood levels of a tumor-expressed miRNA can accurately differentiate between patients with cancer and healthy subjects.

In summary miRNAs have different roles in cancer development and progression, acting as tumour suppressors or oncogenes as well as key activators or suppressors of tumour metastasis. Variations in miRNAs and their target effectors could influence the cell phenotype and disease susceptibility. Thus, identification of the patterns of dysregulated miRNA expression in melanoma provides valuable information to identify novel biomarkers for melanoma diagnosis, disease prognosis and monitoring of therapeutic response.

miRNA Nomenclature

As used herein the numbering of miRNA nomenclature is as follows using the example, hsa-mir-121: The first three letters signify the organism, *Homo sapien*. mir-121 refers to the mature miRNA, miRNA gene and also to the predicted stem-loop portion of the primary transcript. Distinct precursor sequences and genomic loci that express identical mature sequences get names of the form hsa-mir-121-1 and hsa-mir-121-2. Lettered suffixes denote closely related mature sequences—for example hsa-miR-121a and hsa-miR-121b would be expressed from precursors hsa-mir-121a and hsa-mir-121b respectively.

miRNA cloning studies sometimes identify two ~22nt sequences miRNAs which originate from the same predicted precursor. When the relative abundancies clearly indicate which is the predominantly expressed miRNA, the mature sequences are assigned names of the form miR-56 (the predominant product) and miR-56* (from the opposite arm of the precursor). When the data are not sufficient to determine which sequence is the predominant one, names like miR-142-5p (from the 5' arm) and miR-142-3p (from the 3' arm). An older convention sometimes used miR-142-s and miR-142-as.

miRNAs that do not conform to these ideas have in some cases been renamed. There are however a few published exceptions to these rules that are accommodated. For example, different organisms have slightly different naming conventions—in plants, published names are of the form MIR121. Viral miRNAs also adopt a slightly different naming scheme.

miRBase is a searchable database of published miRNA sequences and annotation (www.mirbase.org). Each miRBase Sequence entry has a unique accession number, in addition to a name or ID. The accession number is the only truly stable identifier for an entry—miRNA names may change from those published as relationships between sequences become clear. The advantage of the accessioned system is that such changes can be tracked in the database, allowing names to evolve to remain consistent, whilst providing the user with full access to the data and history.

miRNA Melanoma Biomarkers

A unique collection of miRNA as a genetic classifier expressed in a biological sample is provided that is useful in determining:

the presence or absence and/or staging/prognosis and/or monitoring of treatment of melanoma.

The miRNA useful in the present invention are identified in Tables 1, 2 and 3. These miRNA are identified as having a predictive value to determine whether a subject has melanoma, the stage of melanoma and/or monitoring the treatment of melanoma in a subject. Their expression correlates with the presence of melanoma and/or response to treatment and/or an agent, and more specifically, surgical excision of melanoma and/or a DNA-damage therapeutic agent.

Tables of miRNA

TABLE 1

Diagnosis, Staging and Monitoring

| SEQ ID NO. | MicroRNA ID | MicroRNA Accession | MicroRNA Gene Sequence |
|---|---|---|---|
| 1 | hsa-let-7e-5p | MIMAT0000066 | UGAGGUAGGAGGUUGUAUAGUU |
| 2 | hsa-miR-105-5p | MIMAT0000102 | UCAAAUGCUCAGACUCCUGUGGU |
| 3 | hsa-miR-1180-3p | MIMAT0005825 | UUUCCGGCUCGCGUGGGUGUGU |
| 4 | hsa-miR-1258 | MIMAT0005909 | AGUUAGGAUUAGGUCGUGGAA |
| 5 | hsa-miR-1264 | MIMAT0005791 | CAAGUCUUAUUUGAGCACCUGUU |
| 6 | hsa-miR-1269a | MIMAT0005923 | CUGGACUGAGCCGUGCUACUGG |
| 7 | hsa-miR-127-5p | MIMAT0004604 | CUGAAGCUCAGAGGGCUCUGAU |
| 8 | hsa-miR-1302 | MIMAT0005890 | UUGGGACAUACUUAUGCUAAA |
| 9 | hsa-miR-1306-5p | MIMAT0022726 | CCACCUCCCCUGCAAACGUCCA |
| 10 | hsa-miR-138-5p | MIMAT0000430 | AGCUGGUGUUGUGAAUCAGGCCG |
| 11 | hsa-miR-152-3p | MIMAT0000438 | UCAGUGCAUGACAGAACUUGG |
| 12 | hsa-miR-1537-3p | MIMAT0007399 | AAAACCGUCUAGUUACAGUUGU |

TABLE 1-continued

Diagnosis, Staging and Monitoring

| SEQ ID NO. | MicroRNA ID | MicroRNA Accession | MicroRNA Gene Sequence |
|---|---|---|---|
| 13 | hsa-miR-154-5p | MIMAT0000452 | UAGGUUAUCCGUGUUGCCUUCG |
| 14 | hsa-miR-1-5p | MIMAT0031892 | ACAUACUUCUUUAUAUGCCCAU |
| 15 | hsa-miR-181b-5p | MIMAT0000257 | AACAUUCAUUGCUGUCGGUGGGU |
| 16 | hsa-miR-1910-5p | MIMAT0007884 | CCAGUCCUGUGCCUGCCGCCU |
| 17 | hsa-miR-1973 | MIMAT0009448 | ACCGUGCAAAGGUAGCAUA |
| 18 | hsa-miR-199b-5p | MIMAT0000263 | CCCAGUGUUUAGACUAUCUGUUC |
| 19 | hsa-miR-205-5p | MIMAT0000266 | UCCUUCAUUCCACCGGAGUCUG |
| 20 | hsa-miR-219a-2-3p | MIMAT0004675 | AGAAUUGUGGCUGGACAUCUGU |
| 21 | hsa-miR-2682-5p | MIMAT0013517 | CAGGCAGUGACUGUUCAGACGUC |
| 22 | hsa-miR-27a-3p | MIMAT0000084 | UUCACAGUGGCUAAGUUCCGC |
| 23 | hsa-miR-299-3p | MIMAT0000687 | UAUGUGGGAUGGUAAACCGCUU |
| 24 | hsa-miR-301a-3p | MIMAT0000688 | CAGUGCAAUAGUAUUGUCAAAGC |
| 25 | hsa-miR-3127-5p | MIMAT0014990 | AUCAGGGCUUGUGGAAUGGGAAG |
| 26 | hsa-miR-3131 | MIMAT0014996 | UCGAGGACUGGUGGAAGGGCCUU |
| 27 | hsa-miR-331-3p | MIMAT0000760 | GCCCCUGGGCCUAUCCUAGAA |
| 28 | hsa-miR-337-5p | MIMAT0004695 | GAACGGCUUCAUACAGGAGUU |
| 29 | hsa-miR-34a-5p | MIMAT0000255 | UGGCAGUGUCUUAGCUGGUUGU |
| 30 | hsa-miR-3928-3p | MIMAT0018205 | GGAGGAACCUUGGAGCUUCGGC |
| 31 | hsa-miR-424-5p | MIMAT0001341 | CAGCAGCAAUUCAUGUUUUGAA |
| 32 | hsa-miR-431-5p | MIMAT0001625 | UGUCUUGCAGGCCGUCAUGCA |
| 33 | hsa-miR-450a-5p | MIMAT0001545 | UUUUGCGAUGUGUUCCUAAUAU |
| 34 | hsa-miR-4532 | MIMAT0019071 | CCCCGGGGAGCCCGGCG |
| 35 | hsa-miR-454-3p | MIMAT0003885 | UAGUGCAAUAUUGCUUAUAGGGU |
| 36 | hsa-miR-4787-3p | MIMAT0019957 | GAUGCGCCGCCCACUGCCCCGCGC |
| 37 | hsa-miR-497-5p | MIMAT0002820 | CAGCAGCACACUGUGGUUUGU |
| 38 | hsa-miR-520d-3p | MIMAT0002856 | AAAGUGCUUCUCUUUGGUGGGU |
| 39 | hsa-miR-521 | MIMAT0002854 | AACGCACUUCCCUUUAGAGUGU |
| 40 | hsa-miR-522-3p | MIMAT0002868 | AAAAUGGUUCCCUUUAGAGUGU |
| 41 | hsa-miR-548a-5p | MIMAT0004803 | AAAAGUAAUUGCGAGUUUUACC |
| 42 | hsa-miR-548ad-3p | MIMAT0018946 | GAAAACGACAAUGACUUUUGCA |
| 43 | hsa-miR-548l | MIMAT0005889 | AAAAGUAUUUGCGGGUUUUGUC |
| 44 | hsa-miR-553 | MIMAT0003216 | AAAACGGUGAGAUUUUGUUUU |
| 45 | hsa-miR-624-3p | MIMAT0004807 | CACAAGGUAUUGGUAUUACCU |
| 46 | hsa-miR-652-3p | MIMAT0003322 | AAUGGCGCCACUAGGGUUGUG |
| 47 | hsa-miR-660-5p | MIMAT0003338 | UACCCAUUGCAUAUCGGAGUUG |
| 48 | hsa-miR-764 | MIMAT0010367 | GCAGGUGCUCACUUGUCCUCCU |

TABLE 2

Diagnosis and Monitoring

| SEQ ID NO. | Gene Name | Accession | Sequence |
|---|---|---|---|
| 31 | hsa-miR-424-5p | MIMAT0001341 | CAGCAGCAAUUCAUGUUUUGAA |
| 24 | hsa-miR-301a-3p | MIMAT0000688 | CAGUGCAAUAGUAUUGUCAAAGC |
| 23 | hsa-miR-299-3p | MIMAT0000687 | UAUGUGGGAUGGUAAACCGCUU |
| 15 | hsa-miR-181b-5p | MIMAT0000257 | AACAUUCAUUGCUGUCGGUGGGU |
| 28 | hsa-miR-337-5p | MIMAT0004695 | GAACGGCUUCAUACAGGAGUU |
| 29 | hsa-miR-34a-5p | MIMAT0000255 | UGGCAGUGUCUUAGCUGGUUGU |
| 35 | hsa-miR-454-3p | MIMAT0003885 | UAGUGCAAUAUUGCUUAUAGGGU |
| 32 | hsa-miR-431-5p | MIMAT0001625 | UGUCUUGCAGGCCGUCAUGCA |
| 34 | hsa-miR-4532 | MIMAT0019071 | CCCCGGGGAGCCCGGCG |
| 16 | hsa-miR-1910-5p | MIMAT0007884 | CCAGUCCUGUGCCUGCCGCCU |
| 22 | hsa-miR-27a-3p | MIMAT0000084 | UUCACAGUGGCUAAGUUCCGC |
| 37 | hsa-miR-497-5p | MIMAT0002820 | CAGCAGCACACUGUGGUUUGU |
| 41 | hsa-miR-548a-5p | MIMAT0004803 | AAAAGUAAUUGCGAGUUUUACC |
| 11 | hsa-miR-152-3p | MIMAT0000438 | UCAGUGCAUGACAGAACUUGG |
| 12 | hsa-miR-1537-3p | MIMAT0007399 | AAAACCGUCUAGUUACAGUUGU |
| 4 | hsa-miR-1258 | MIMAT0005909 | AGUUAGGAUUAGGUCGUGGAA |
| 13 | hsa-miR-154-5p | MIMAT0000452 | UAGGUUAUCCGUGUUGCCUUCG |
| 33 | hsa-miR-450a-5p | MIMAT0001545 | UUUUGCGAUGUGUUCCUAAUAU |
| 21 | hsa-miR-2682-5p | MIMAT0013517 | CAGGCAGUGACUGUUCAGACGUC |
| 42 | hsa-miR-548ad-3p | MIMAT0018946 | GAAAACGACAAUGACUUUUGCA |
| 20 | hsa-miR-219a-2-3p | MIMAT0004675 | AGAAUUGUGGCUGGACAUCUGU |
| 36 | hsa-miR-4787-3p | MIMAT0019957 | GAUGCGCCGCCCACUGCCCCGCGC |
| 38 | hsa-miR-520d-3p | MIMAT0002856 | AAAGUGCUUCUCUUUGGUGGGU |
| 40 | hsa-miR-522-3p | MIMAT0002868 | AAAAUGGUUCCCUUUAGAGUGU |
| 6 | hsa-miR-1269a | MIMAT0005923 | CUGGACUGAGCCGUGCUACUGG |
| 19 | hsa-miR-205-5p | MIMAT0000266 | UCCUUCAUUCCACCGGAGUCUG |
| 44 | hsa-miR-553 | MIMAT0003216 | AAAACGGUGAGAUUUUGUUUU |
| 26 | hsa-miR-3131 | MIMAT0014996 | UCGAGGACUGGUGGAAGGGCCUU |
| 5 | hsa-miR-1264 | MIMAT0005791 | CAAGUCUUAUUUGAGCACCUGUU |
| 48 | hsa-miR-764 | MIMAT0010367 | GCAGGUGCUCACUUGUCCUCCU |
| 30 | hsa-miR-3928-3p | MIMAT0018205 | GGAGGAACCUUGGAGCUUCGGC |
| 43 | hsa-miR-5481 | MIMAT0005889 | AAAAGUAUUUGCGGGUUUUGUC |
| 10 | hsa-miR-138-5p | MIMAT0000430 | AGCUGGUGUUGUGAAUCAGGCCG |
| 17 | hsa-miR-1973 | MIMAT0009448 | ACCGUGCAAAGGUAGCAUA |
| 45 | hsa-miR-624-3p | MIMAT0004807 | CACAAGGUAUUGGUAUUACCU |
| 9 | hsa-miR-1306-5p | MIMAT0022726 | CCACCUCCCCUGCAAACGUCCA |

TABLE 2-continued

Diagnosis and Monitoring

| SEQ ID NO. | Gene Name | Accession | Sequence |
|---|---|---|---|
| 14 | hsa-miR-1-5p | MIMAT0031892 | ACAUACUUCUUUAUAUGCCCAU |
| 8 | hsa-miR-1302 | MIMAT0005890 | UUGGGACAUACUUAUGCUAAA |

TABLE 3

Staging

| SEQ ID NO | MicroRNA | MicroRNA Accession | Sequence |
|---|---|---|---|
| 18 | hsa-miR-199b-5p | MIMAT0000263 | CCCAGUGUUUAGACUAUCUGUUC |
| 47 | hsa-miR-660-5p | MIMAT0003338 | UACCCAUUGCAUAUCGGAGUUG |
| 28 | hsa-miR-337-5p | MIMAT0004695 | GAACGGCUUCAUACAGGAGUU |
| 1 | hsa-let-7e-5p | MIMAT0000066 | UGAGGUAGGAGGUUGUAUAGUU |
| 46 | hsa-miR-652-3p | MIMAT0003322 | AAUGGCGCCACUAGGGUUGUG |
| 27 | hsa-miR-331-3p | MIMAT0000760 | GCCCCUGGGCCUAUCCUAGAA |
| 12 | hsa-miR-1537-3p | MIMAT0007399 | AAAACCGUCUAGUUACAGUUGU |
| 24 | hsa-miR-301a-3p | MIMAT0000688 | CAGUGCAAUAGUAUUGUCAAAGC |
| 22 | hsa-miR-27a-3p | MIMAT0000084 | UUCACAGUGGCUAAGUUCCGC |
| 13 | hsa-miR-154-5p | MIMAT0000452 | UAGGUUAUCCGUGUUGCCUUCG |
| 23 | hsa-miR-299-3p | MIMAT0000687 | UAUGUGGGAUGGUAAACCGCUU |
| 11 | hsa-miR-152-3p | MIMAT0000438 | UCAGUGCAUGACAGAACUUGG |
| 2 | hsa-miR-105-5p | MIMAT0000102 | UCAAAUGCUCAGACUCCUGUGGU |
| 7 | hsa-miR-127-5p | MIMAT0004604 | CUGAAGCUCAGAGGGCUCUGAU |
| 39 | hsa-miR-521 | MIMAT0002854 | AACGCACUUCCCUUUAGAGUGU |
| 36 | hsa-miR-4787-3p | MIMAT0019957 | GAUGCGCCGCCCACUGCCCCGCGC |
| 3 | hsa-miR-1180-3p | MIMAT0005825 | UUUCCGGCUCGCGUGGGUGUGU |
| 25 | hsa-miR-3127-5p | MIMAT0014990 | AUCAGGGCUUGUGGAAUGGGAAG |

Measuring miRNA Expression Using Classification Models

A variety of methods have been utilized in an attempt to identify miRNA and diagnose disease. For nucleic acid markers, these include mRNA expression profiles, microRNA profiles, FISH, serial analysis of gene expression (SAGE), methylation profiles, gene expression arrays, and sequencing methods (eg. NGS).

Expression Levels

In the present context the terms "level of expression of a microRNA" and "level of a microRNA" are used synonymously as a measure of the "amount of a specific microRNA" that is detected in the sample. The term "expression" may be expressed in either absolute or relative measures and refers to values obtained by both quantitative, as well as qualitative methods.

The term "expression level" refers to a miRNA whose expression is activated to a higher or lower level in a subject suffering from a specific disease, relative to its expression in a normal subject, or relative to its expression in a patient that responds differently to a particular therapy or has a different prognosis. The terms also include miRNA whose expression is activated to a higher or lower level at different stages of the same disease. It is also understood that a differentially expressed miRNA may be either activated or inhibited at the nucleic acid level or RNA level, or may be subject to alternative splicing to result in a different RNA product.

miRNA "expression levels" may include a comparison of expression between two or more miRNA or their gene products; or a comparison of the ratios of the expression between two or more miRNA or their miRNA products; or even a comparison of two differently processed products of the same gene, which differ between normal subjects and subjects suffering from a disease; or between various stages of the same disease. miRNA expression levels includes both quantitative, as well as qualitative, differences in the temporal or cellular expression pattern in a miRNA among, for example, normal and diseased cells, or among cells which have undergone different disease events or disease stages.

One way of quantification is described in the Examples i.e. NanoString nCounter Analysis System. Nanostring is an amplification-free technology that measures nucleic acid content by counting molecules directly. However, the miRNA may be quantified in a multitude of other ways e.g. by microarrays, next generation sequencing, qRT-PCR, digital-PCR, northern blots, dot blots, RN'ase protection assays, quantitative mass spectroscopy or various quantitative PCR-based methods such as the TaqMan assay or the UniRT assay used in the examples.

In certain example embodiments, all or a portion of the miRNA recited in Table 1 and/or 2 and/or 3 may be used in a classification score, staging score and/or miRNA expression signature. For example, a classification score, staging score and/or miRNA expression signature comprising the miRNA in Table 1, 2 or 3 can be generated using the methods provided herein and can comprise between one, and all of the markers set forth in Table 1, 2 or 3 and each and every combination in between (e.g., 17 selected markers, 18 selected markers, 22 selected markers, 28 selected markers, 32 selected markers, 38 selected markers, 48 selected markers, etc.). In some embodiments, the expression signature comprises at least 17, 18, 20, 22, 28, 30, 38, 40, or 48 markers. In other embodiments, the expression signature comprises no more than 17, 18, 20, 22, 28, 30, 38, 40, or 48, markers. In one example embodiment, classification score, staging score and/or miRNA expression signature includes a plurality of markers listed in Table 1, 2 or 3. In some embodiments the expression signature includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1, 2 or 3. Selected classification scores, staging scores and/or miRNA expression signatures can be assembled from the miRNA provided using methods described herein and analogous methods known in the art. In one embodiment, the classification score, staging score and/or miRNA a expression signature contains all miRNA in Table 1, 2 or 3. Preferred miRNA are:

(a) hsa-miR-424-5p, hsa-miR-301a-3p, hsa-miR-299-3p, hsa-miR-181b-5p, hsa-miR-337-5p, hsa-miR-34a-5p, hsa-miR-454-3p, hsa-miR-431-5p, hsa-miR-4532, hsa-miR-1910-5p, hsa-miR-27a-3p, hsa-miR-497-5p, hsa-miR-548a-5p, hsa-miR-152-3p, hsa-miR-1537-3p, hsa-miR-1258, hsa-miR-154-5p, hsa-miR-450a-5p, hsa-miR-2682-5p, hsa-miR-548ad-3p, hsa-miR-219a-2-3p, hsa-miR-4787-3p, hsa-miR-520d-3p, hsa-miR-522-3p, hsa-miR-1269a, hsa-miR-205-5p, hsa-miR-553, hsa-miR-3131, hsa-miR-1264, hsa-miR-764, hsa-miR-3928-3p, hsa-miR-548l, hsa-miR-138-5p, hsa-miR-1973, hsa-miR-624-3p, hsa-miR-1306-5p, hsa-miR-1-5p, hsa-miR-1302;

(b) hsa-miR-199b-5p, hsa-miR-660-5p, hsa-miR-337-5p, hsa-let-7e-5p, hsa-miR-652-3p, hsa-miR-331-3p, hsa-miR-1537-3p, hsa-miR-301a-3p, hsa-miR-27a-3p, hsa-miR-154-5p, hsa-miR-299-3p, hsa-miR-152-3p, hsa-miR-105-5p, hsa-miR-127-5p, hsa-miR-521, hsa-miR-4787-3p, hsa-miR-1180-3p, hsa-miR-3127-5p (c) hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p and hsa-miR-431-5p.

In other embodiments further markers can be used to improve the accuracy of a classification score, staging score and/or miRNA expression signature. In certain example embodiments, a classification score, staging score and/or miRNA a expression signature comprising the miRNA in Table 1, 2 or 3 can be generated using the methods provided herein and can comprise all of the markers set forth in Table 1, 2 or 3 and each and further markers up to 800 markers. In some embodiments, the expression signature comprises at least 48, 50, 100, 150, 200, 250, 300, 350, 400, 450, 500, 550, 600, 650, 700, 750 or 800 markers. In some embodiments the expression signature includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1, 2 or 3. Selected classification scores, staging scores and/or miRNA expression signatures can be assembled from the miRNA provided using methods described herein and analogous methods known in the art.

Dataset

The term "dataset" refers to a matrix of individual patient RNA compared with 800 microRNA gene expression values, generated by isolating RNA from cell-free plasma and performing Nanostring nCounter gene expression analysis. The control is the level of the at least one miRNA gene product from a subject that does not have the disorder. The size of the dataset will vary depending on the type of genes and patients analysed. Relevant factors include the sensitivity of the technology platform and magnitude and consistency of the difference in gene expression between conditions or disease states.

Measuring Classification Score

Mathematical Models

Creating a miRNA Expression Classification Score

The patient training set data is preferably derived from tissue samples having been characterized by diagnosis, disease stage, prognosis, likelihood of recurrence, long term survival, clinical outcome, treatment response, cancer classification and genetic or molecular status. Expression profiles, and corresponding decision scores from patient samples may be correlated with the characteristics of patient samples in the training set that are on the same side of the mathematically derived score decision threshold. The threshold of the classifier scalar output is optimized to maximize the sum of sensitivity and specificity under cross-validation as observed within the training dataset.

Melanoma Staging

Melanoma progression is classified using the following clinical staging:

Stage 0: The melanoma is confined to the cells in the top layer of the skin (epidermis) and has not invaded the deeper layers (dermis). It is also known as in situ melanoma.
Treatment: Surgical removal Stage 1: melanoma can be defined in two ways: 2 mm without ulceration, metastases or lymph node involvement; or up to 1 mm with ulceration, but without metastases or lymph node involvement.
Treatment: Surgical removal. The removal of nearby lymph nodes may also be considered if the melanoma is between 1-4 mm thick and/or shows signs of rapid growth.

Stage 2: melanoma is defined by thickness and ulceration. There is no lymph node involvement or spread to organs.
Treatment: Surgical removal is the main treatment, however the removal of nearby lymph nodes is also a treatment option to prevent further spread. Drug treatment or radiation may also be required to lower the risk of the cancer returning.

Stage 3: melanoma can be any thickness and lymph nodes have become involved.

Treatment: Surgical removal of the lymph nodes is usually required. Drug treatment and radiation may also be considered.

Stage 4: melanoma can be any thickness and has spread to distant lymph nodes and organs e.g. lungs, liver, brain or bone.

Treatment: Systematic drug therapies including immunotherapy, chemotherapy and targeted therapy. Surgery and radiation may also be used to relieve symptoms.

Determining the stage of melanoma may be carried out after the subject is diagnosed with melanoma according to the method of the invention, or before a subject is diagnosed, provided that the staging is determined according to the presence of at least one miRNAs from Table 3 (MEL18).

Measuring Staging Score

Genes in the MEL18 (Table 3) staging signature can be used to assess the stage of an individual's melanoma progression by methods including logistic regression, multi-class algorithms (I vs II vs III vs IV) such as KNN, nearest centroid or SVM, or binary decision-tree methods (eg I vs 4, 4 vs 3, 1 vs 2, 3 vs 3).

Monitoring Status of Disease

Although the preferred method is to detect the expression of miRNA for the purpose of diagnosing melanoma development, the detection of converse changes in the levels of said miRNA may be desired under certain circumstances, for example, to monitor the effectiveness of therapeutic, adjuvant or prophylactic treatment directed to modulating a melanoma condition.

The method of the present invention is therefore useful as a one off test or as an on-going monitor of those individuals thought to be at risk of melanoma development and/or as a monitor of the effectiveness of therapeutic and/or prophylactic treatment regimes directed to inhibiting or otherwise slowing melanoma development. In these situations, mapping the modulation of miRNA expression levels in any one or more classes of biological samples is a valuable indicator of the status of an individual and/or the effectiveness of a therapeutic and/or prophylactic regime which is currently in use. Accordingly, the method of the present invention should be understood to extend to monitoring the status of melanoma in a subject based on the value of the classification score and comparing to a previous classification score.

Monitoring Treatment Response

In monitoring the effectiveness of therapeutic or prophylactic treatment regimes directed to inhibiting or otherwise slowing melanoma development, one may assess the modulation of miRNA expression levels. For example, screening for a classification score subsequent to the onset of a therapeutic regime which may be utilised to indicate reversal or other forms of improvement of the subject individual's condition. Conversely, a modulation in miRNA expression levels may indicate the presence and/or increased staging and/or no change in staging of the melanoma which is indicative of an adverse melanoma outcome.

The term "adverse melanoma outcome" refers to screening for a classification score subsequent to the onset of a therapeutic regime, comparing the classification score to a previous classification score and/or other clinical assessment and determining a modulation in miRNA expression levels which may indicate the presence of melanoma and/or increased disease progression and/or no change in the patient's condition.

Method of Treatment

As used herein, the terms 'treating' or 'treatment' include administering a therapeutically effective amount of an agent and/or surgical excision of melanoma described herein sufficient to reduce or eliminate at least one symptom of a specified disease or condition. In an embodiment, the disease or condition of the current invention is melanoma.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

Agents/Therapeutics

The term 'agent' means any molecule, including polypeptides, antibodies, polynucleotides, chemical compounds and small molecules. In particular the term agent includes compounds such as test compounds or drug candidate compounds.

Suitable compounds for inhibiting miRNA gene expression include double-stranded RNA (such as short- or small-interfering RNA or "siRNA"), antisense nucleic acids, antagonist microRNAs, such as, antagomirs, and enzymatic RNA molecules, such as ribozymes. Each of these compounds can be targeted to a given miRNA gene product and interfere with the expression of (e.g., inhibit translation of, induce cleavage or destruction of) the target miRNA gene product.

For example, expression of a given miRNA gene can be inhibited by inducing RNA interference of the miRNA gene with an isolated double-stranded RNA ("dsRNA") molecule which has at least 90%, for example at least 95%, at least 98%, at least 99%, or 100%, sequence homology with at least a portion of the miRNA gene product. In a particular embodiment, the dsRNA molecule is a short or small interfering RNA or siRNA. siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miRNA gene product.

Antagomirs or "antagonist microRNA", as used herein, refer to engineered oligonucleotides (sometimes together with chemical modifications) that are used to antagonize miRNA functions, based on complementation and hybridization.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

Expression of a given mlRNA gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g. RNA, DNA, RNA-DNA chimeras, peptide nucleic acid (PNA)) that generally comprise a nucleic acid sequence complementary to a contiguous nucleic acid sequence in a miRNA gene product. The antisense nucleic acid can comprise a nucleic acid sequence that is 50-100% complementary, 75-100% complementary, or 95-100% complementary to a contiguous nucleic acid sequence in a miRNA gene product. Without wishing to be bound by any theory, it is believed that the antisense nucleic acids activate RNase H or another cellular nuclease that digests the miRNA gene product/antisense nucleic acid duplex.

Expression of a given miRNA gene can also be inhibited by an enzymatic nucleic acid. As used herein, an "enzymatic nucleic acid" refers to a nucleic acid comprising a substrate binding region that has complementarity to a contiguous nucleic acid sequence of a miRNA gene product, and which is able to specifically cleave the miRNA gene product. The enzymatic nucleic acid substrate binding region can be, for example, 50-100% complementary, 75-100% complementary, or 95-100% complementary to a contiguous nucleic acid sequence in a miRNA gene product. The enzymatic nucleic acids can also comprise modifications at the base, sugar, and/or phosphate groups. An exemplary enzymatic nucleic acid for use in the present methods is a ribozyme.

'Therapeutically effective amount' means that amount of a drug, compound, antimicrobial, antibody, or pharmaceutical agent that will elicit the biological or medical response of a subject that is being sought by a medical doctor or other clinician. In particular, with regard to melanoma, the term "effective amount" is intended to include an effective amount of a compound or agent which modifies the level of at least one miRNA in said subject.

In an embodiment, the present invention provides a method for treating melanoma in a subject comprising administering to said subject a therapeutically effective amount of an agent wherein said agent modifies directly or indirectly the expression level of at least one miRNA, wherein said at least one miRNA is selected from:

hsa-miR-424-5p, hsa-miR-301a-3p, hsa-miR-299-3p, hsa-miR-181b-5p, hsa-miR-337-5p, hsa-miR-34a-5p, hsa-miR-454-3p, hsa-miR-431-5p, hsa-miR-4532, hsa-miR-1910-5p, hsa-miR-27a-3p, hsa-miR-497-5p, hsa-miR-548a-5p, hsa-miR-152-3p, hsa-miR-1537-3p, hsa-miR-1258, hsa-miR-154-5p, hsa-miR-450a-5p, hsa-miR-2682-5p, hsa-miR-548ad-3p, hsa-miR-219a-2-3p, hsa-miR-4787-3p, hsa-miR-520d-3p, hsa-miR-522-3p, hsa-miR-1269a, hsa-miR-205-5p, hsa-miR-553, hsa-miR-3131, hsa-miR-1264, hsa-miR-764, hsa-miR-3928-3p, hsa-miR-548l, hsa-miR-138-5p, hsa-miR-1973, hsa-miR-624-3p, hsa-miR-1306-5p, hsa-miR-1-5p, hsa-miR-1302, hsa-miR-199b-5p, hsa-miR-660-5p, hsa-let-7e-5p, hsa-miR-652-3p, hsa-miR-331-3p, hsa-miR-105-5p, hsa-miR-127-5p, hsa-miR-521, hsa-miR-1180-3p, hsa-miR-3127-5p.

In an embodiment, the method for treating melanoma in a subject comprising administering to said subject a therapeutically effective amount of an agent wherein said agent modifies directly or indirectly the expression level of miRNA wherein said miRNA consist of:

hsa-miR-424-5p, hsa-miR-301a-3p, hsa-miR-299-3p, hsa-miR-181b-5p, hsa-miR-337-5p, hsa-miR-34a-5p, hsa-miR-454-3p, hsa-miR-431-5p, hsa-miR-4532, hsa-miR-1910-5p, hsa-miR-27a-3p, hsa-miR-497-5p, hsa-miR-548a-5p, hsa-miR-152-3p, hsa-miR-1537-3p, hsa-miR-1258, hsa-miR-154-5p, hsa-miR-450a-5p, hsa-miR-2682-5p, hsa-miR-548ad-3p, hsa-miR-219a-2-3p, hsa-miR-4787-3p, hsa-miR-520d-3p, hsa-miR-522-3p, hsa-miR-1269a, hsa-miR-205-5p, hsa-miR-553, hsa-miR-3131, hsa-miR-1264, hsa-miR-764, hsa-miR-3928-3p, hsa-miR-548l, hsa-miR-138-5p, hsa-miR-1973, hsa-miR-624-3p, hsa-miR-1306-5p, hsa-miR-1-5p, hsa-miR-1302;

In an embodiment, the method for treating melanoma in a subject comprising administering to said subject a therapeutically effective amount of an agent wherein said agent modifies directly or indirectly the expression level of miRNA wherein said miRNA consist of:

hsa-miR-199b-5p, hsa-miR-660-5p, hsa-miR-337-5p, hsa-let-7e-5p, hsa-miR-652-3p, hsa-miR-331-3p, hsa-miR-1537-3p, hsa-miR-301a-3p, hsa-miR-27a-3p, hsa-miR-154-5p, hsa-miR-299-3p, hsa-miR-152-3p, hsa-miR-105-5p, hsa-miR-127-5p, hsa-miR-521, hsa-miR-4787-3p, hsa-miR-1180-3p, hsa-miR-3127-5p In an embodiment, the method for treating melanoma in a subject comprising administering to said subject a therapeutically effective amount of an agent wherein said agent modifies directly or indirectly the expression level of miRNA wherein said miRNA consist of:

hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p and hsa-miR-431-5p.

In another embodiment, said agent is one or more of the following:
(i) siRNA
(ii) antisense nucleic acids,
(iii) antagonist microRNAs, including: antagomirs
(iv) enzymatic RNA molecules, including: ribozymes
(v) miRNA agonist
(vi) anti-miRNA antibodies
(vii) Aldesleukin
(viii) Cobimetinib
(ix) Cotellic (Cobimetinib)
(x) Dabrafenib
(xi) Dacarbazine
(xii) DTIC-Dome (Dacarbazine)
(xiii) IL-2 (Aldesleukin)
(xiv) Imlygic (Talimogene Laherparepvec)
(xv) Interleukin-2 (Aldesleukin)
(xvi) Intron A (Recombinant Interferon Alfa-2b)
(xvii) Ipilimumab
(xviii) Keytruda (Pembrolizumab)
(xix) Mekinist (Trametinib)
(xx) Nivolumab
(xxi) Opdivo (Nivolumab)
(xxii) Peginterferon Alfa-2b
(xxiii) PEG-Intron (Peginterferon Alfa-2b)
(xxiv) Pembrolizumab
(xxv) Proleukin (Aldesleukin)
(xxvi) Recombinant Interferon Alfa-2b
(xxvii) Sylatron (Peginterferon Alfa-2b)

(xxviii) Tafinlar (Dabrafenib)
(xxix) Talimogene Laherparepvec
(xxx) Trametinib
(xxxi) Vemurafenib
(xxxii) Yervoy (Ipilimumab)
(xxxiii) Zelboraf (Vemurafenib)

In a further embodiment, the present invention provides the use of an agent which modifies directly or indirectly the expression level of at least one miRNA for the production of a medicament effective in the treatment of melanoma wherein said at least one microRNA is selected from:

hsa-miR-424-5p, hsa-miR-301a-3p, hsa-miR-299-3p, hsa-miR-181b-5p, hsa-miR-337-5p, hsa-miR-34a-5p, hsa-miR-454-3p, hsa-miR-431-5p, hsa-miR-4532, hsa-miR-1910-5p, hsa-miR-27a-3p, hsa-miR-497-5p, hsa-miR-548a-5p, hsa-miR-152-3p, hsa-miR-1537-3p, hsa-miR-1258, hsa-miR-154-5p, hsa-miR-450a-5p, hsa-miR-2682-5p, hsa-miR-548ad-3p, hsa-miR-219a-2-3p, hsa-miR-4787-3p, hsa-miR-520d-3p, hsa-miR-522-3p, hsa-miR-1269a, hsa-miR-205-5p, hsa-miR-553, hsa-miR-3131, hsa-miR-1264, hsa-miR-764, hsa-miR-3928-3p, hsa-miR-548l, hsa-miR-138-5p, hsa-miR-1973, hsa-miR-624-3p, hsa-miR-1306-5p, hsa-miR-1-5p, hsa-miR-1302, hsa-miR-199b-5p, hsa-miR-660-5p, hsa-let-7e-5p, hsa-miR-652-3p, hsa-miR-331-3p, hsa-miR-105-5p, hsa-miR-127-5p, hsa-miR-521, hsa-miR-1180-3p, hsa-miR-3127-5p.

In an embodiment, the use of an agent which modifies directly or indirectly the expression level of miRNA wherein said miRNA consist of:

hsa-miR-424-5p, hsa-miR-301a-3p, hsa-miR-299-3p, hsa-miR-181b-5p, hsa-miR-337-5p, hsa-miR-34a-5p, hsa-miR-454-3p, hsa-miR-431-5p, hsa-miR-4532, hsa-miR-1910-5p, hsa-miR-27a-3p, hsa-miR-497-5p, hsa-miR-548a-5p, hsa-miR-152-3p, hsa-miR-1537-3p, hsa-miR-1258, hsa-miR-154-5p, hsa-miR-450a-5p, hsa-miR-2682-5p, hsa-miR-548ad-3p, hsa-miR-219a-2-3p, hsa-miR-4787-3p, hsa-miR-520d-3p, hsa-miR-522-3p, hsa-miR-1269a, hsa-miR-205-5p, hsa-miR-553, hsa-miR-3131, hsa-miR-1264, hsa-miR-764, hsa-miR-3928-3p, hsa-miR-548l, hsa-miR-138-5p, hsa-miR-1973, hsa-miR-624-3p, hsa-miR-1306-5p, hsa-miR-1-5p, hsa-miR-1302;

In an embodiment, the use of an agent which modifies directly or indirectly the expression level of miRNA wherein said miRNA consist of:

hsa-miR-199b-5p, hsa-miR-660-5p, hsa-miR-337-5p, hsa-let-7e-5p, hsa-miR-652-3p, hsa-miR-331-3p, hsa-miR-1537-3p, hsa-miR-301a-3p, hsa-miR-27a-3p, hsa-miR-154-5p, hsa-miR-299-3p, hsa-miR-152-3p, hsa-miR-105-5p, hsa-miR-127-5p, hsa-miR-521, hsa-miR-4787-3p, hsa-miR-1180-3p, hsa-miR-3127-5p In an embodiment, the use of an agent which modifies directly or indirectly the expression level of miRNA wherein said miRNA consist of:

hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p and hsa-miR-431-5p.

Relapse or Recurrence

When melanoma comes back after it has been treated, it is called a relapse or recurrence. Recurrent melanoma may appear locally (at or near the site of the original primary melanoma tumor), or in another part of the body. Melanoma can come back as many as 10 or more years after it was first treated. This is not the same as developing a new primary melanoma that is unrelated to the first primary melanoma.

The present invention provides a method of monitoring the status of melanoma for relapse or recurrence in a subject previously diagnosed with melanoma, said method comprising (i) detecting microRNA expression levels in a biological sample, (ii) calculating a classification score (CS) of the biological sample based on one or more algorithms from a dataset comprising the expression levels of said microRNAs, and (iii) classifying the biological melanoma or not based on the value of the classification score and comparing to a previously determined classification threshold, which separates those with melanoma from those without wherein the microRNA comprise at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In an embodiment, said microRNA consist of:

hsa-let-7e-5p,
hsa-miR-105-5p,
hsa-miR-1180-3p,
hsa-miR-1258, hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In a further embodiment, said microRNA consist of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-764

In yet another embodiment, said microRNA consist of:

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p Detection Methods: Kits/Arrays
Platforms for microRNA Profiling An important factor in developing a novel genetic test is the selection of a detection technology that offers high sensitivity and specificity for the target genes of interest. In a clinical setting, the platform should be automatable and able to analyse multiple samples in parallel. Options include
  (i) quantitative, real-time or digital droplet PCR, long thought of as the 'gold standard' and used for assays such as Oncotype DX (Genomic Health, Redwood CA);
  (ii) array-based methods such as Agilent or Affymetrix microarrays (used for MammaPrint (Agendia, Irvine CA) and MyPRS assays (Signal Genetics, San Diego, CA,)
  (iii) methods such as RNA-seq (eg. Illumina, CA) and nCounter (Nanostring, WA), which generate count-based measurements of gene abundance.
  (iv) or immobilized probe for the detection of microRNA or the resources for sample analysis commonly used for analysis of short RNAs in next generation sequencing experiment.

The terms "Q-PCR" or "q-PCR" refers to quantitative polymerase chain reaction. Q-PCR is a highly sensitive method for quantifying the amounts of specific DNA (and RNA) species in a test sample. As quantification of RNA by the PCR technique requires that the RNA is reverse transcribed it is often referred to as "qRT-PCR" or "RT-Q-PCR" to indicate that quantitative PCR is used to quantify specific RNAs. A thorough treatise of the Q-PCR and qRT-PCR techniques can be found in Bustin, S. A. (ed.) A-Z of quantitative PCR, IUL Biotechnology Series 5 (2004) 882 pages, which is incorporated herein by reference.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for prognostic or diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Biological sample" as used herein may mean a sample of biological tissue or fluid that comprises miRNA. Such samples include fluid which is blood, plasma or serum, particularly plasma. Such samples include, but are not limited to, tissue isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

As used herein, the term "subject" can be any animal. In one example, the animal is a vertebrate. For example, the animal can be a mammal, avian, arthropod, chordate, amphibian or reptile. Exemplary subjects include but are not limited to human, primate, livestock (e.g. sheep, cow, chicken, horse, donkey, pig), companion animals (e.g. dogs, cats), laboratory test animals (e.g. mice, rabbits, rats, guinea pigs, hamsters), captive wild animal (e.g. fox, deer). In one example, the mammal is a human.

In an embodiment, the present invention provides a molecular array, comprising a plurality of:
(i) nucleic acid molecules comprising a nucleotide sequence corresponding to any one or more of the microRNA listed in Table 1 or a sequence exhibiting at least 80% identity thereto or a functional derivative, fragment, variant or homologue of said nucleic acid molecule; or
(ii) nucleic acid molecules comprising a nucleotide sequence capable of hybridising to any one or more of the sequences of (i) under medium stringency conditions or a functional derivative, fragment, variant or homologue of said nucleic acid molecule; or
(iii) nucleic acid probes or oligonucleotides comprising a nucleotide sequence capable of hybridising to any one or more of the sequences of (i) under medium stringency conditions or a functional derivative, fragment, variant or homologue of said nucleic acid molecule;
wherein the level of expression of said microRNA of (i)-(iii) is used to calculate a classification score (CS) which is indicative of the presence or absence of melanoma in a subject or a staging score (SS) which is indicative of the stage of melanoma in a subject.

Preferably, said percentage identity is at least 85%, 90%, 91%, 92%, 93%, 94%, 95%, 96%, 97%, 98% or 99%.

Low stringency includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.0 1M to at least about 0.15M salt for hybridisation, and at least about 0.01M to at least about 0.15M salt for washing conditions. In general, washing is carried out at Tm=69.3+0.41 (G+C) %=−12° C. However, the Tm of a duplex DNA decreases by 1° C. with every increase of 1% in the number of mismatched based pairs (Bonner et al (1973) J. Mol. Biol. 81: 123).

In an embodiment, the present invention provides a diagnostic kit for the assessment of diagnosis of a melanoma, assessment of disease stage and assessment of a subject and/or disease susceptibility to the proposed treatment comprising:
(a) at least one "forward" amplification primer;
(b) at least one "reverse" amplification primer; and
(c) at least one probe for the capture and/or detection of microRNA or
(d) immobilized probe(s) for the detection of microRNA or the resources for sample analysis commonly used for analysis of short RNAs in next generation sequencing experiment wherein the primers are designed in such a way that they enable specific amplification of the nucleotide sequences of at least one microRNA selected from:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p, hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p,
hsa-miR-652-3p,
hsa-miR-660-5p,
hsa-miR-764

In an embodiment, said microRNA consist of:

hsa-let-7e-5p,
hsa-miR-105-5p,
hsa-miR-1180-3p,
hsa-miR-1258,
hsa-miR-1264,
hsa-miR-1269a,
hsa-miR-127-5p,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-199b-5p,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3127-5p.
hsa-miR-3131,
hsa-miR-331-3p,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-521,
hsa-miR-522-3p,
hsa-miR-548a-5p,
hsa-miR-548ad-3p,
hsa-miR-548l,
hsa-miR-553,
hsa-miR-624-3p, hsa-miR-652-3p,
hsa-miR-660-5p,
hsa-miR-764

In a further embodiment, said microRNA consist of:

hsa-miR-1258,
hsa-miR-1264,
hsa-miR-1269a,
hsa-miR-1302,
hsa-miR-1306-5p,
hsa-miR-138-5p,
hsa-miR-152-3p,
hsa-miR-1537-3p,
hsa-miR-154-5p,
hsa-miR-1-5p,
hsa-miR-181b-5p,
hsa-miR-1910-5p,
hsa-miR-1973,
hsa-miR-205-5p,
hsa-miR-219a-2-3p,
hsa-miR-2682-5p,
hsa-miR-27a-3p,
hsa-miR-299-3p,
hsa-miR-301a-3p,
hsa-miR-3131,
hsa-miR-337-5p,
hsa-miR-34a-5p,
hsa-miR-3928-3p,
hsa-miR-424-5p,
hsa-miR-431-5p,
hsa-miR-450a-5p,
hsa-miR-4532,
hsa-miR-454-3p,
hsa-miR-4787-3p,
hsa-miR-497-5p,
hsa-miR-520d-3p,
hsa-miR-522-3p,
hsa-miR-548a-5p,
hsa-miR-548ad-3p,
hsa-miR-548l,
hsa-miR-553,
hsa-miR-624-3p,
hsa-miR-76

In yet another embodiment, said microRNA consist of:

hsa-miR-1258,
hsa-miR-1264,
hsa-miR-1302,
hsa-miR-152-3p,
hsa-miR-154-5p,
hsa-miR-181b-5p,
hsa-miR-1910-5p,
hsa-miR-219a-2-3p,
hsa-miR-299-3p,
hsa-miR-34a-5p,
hsa-miR-424-5p,
hsa-miR-431-5p.
hsa-miR-4532,
hsa-miR-454-3p,
hsa-miR-497-5p,
hsa-miR-548a-5p,
hsa-miR-548ad-3p In another embodiment, said microRNA consist of:

hsa-let-7e-5p,
hsa-miR-105-5p,
hsa-miR-1180-3p,
hsa-miR-127-5p,
hsa-miR-152-3p, hsa-miR-1537-3p,
hsa-miR-154-5p,
hsa-miR-199b-5p,
hsa-miR-27a-3p,
hsa-miR-299-3p,
hsa-miR-301a-3p,
hsa-miR-3127-5p.
hsa-miR-331-3p,
hsa-miR-337-5p,
hsa-miR-4787-3p,
hsa-miR-521,
hsa-miR-652-3p,
hsa-miR-660-

In an embodiment, the subject is a human.

In one embodiment of the present disclosure, the capture probes are immobilized on an array. By "array" is intended a solid support or a substrate with peptide or nucleic acid probes attached to the support or substrate. Arrays typically comprise a plurality of different capture probes that are coupled to a surface of a substrate in different, known locations. The arrays of the disclosure comprise a substrate having a plurality of capture probes that can specifically bind an intrinsic gene expression product.

The array may be fabricated on a surface of virtually any shape or even a multiplicity of surfaces. Arrays may be probes (e.g., nucleic-acid binding probes) on beads, gels, polymeric surfaces, fibers such as fiber optics, glass or any other appropriate substrate Arrays may be packaged in such a manner as to allow for diagnostics or other manipulation on the device.

In another embodiment, the kit comprises a set of oligonucleotide primers sufficient for the detection and/or quantitation of each of the intrinsic genes listed in Table 1, 2 or 3. The oligonucleotide primers may be provided in a lyophilized or reconstituted form, or may be provided as a set of nucleotide sequences. The kit may further comprise reagents and instructions sufficient for the amplification of expression products from the genes listed in Table 1, 2 or 3.

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Regardless of whether the expression patterns initially recorded are analog or digital in nature, the expression patterns, expression profiles (collective expression patterns), and molecular signatures (correlated expression patterns) are stored digitally and accessed via a database. Typically, the database is compiled and maintained at a central facility, with access being available locally and/or remotely.

The present invention is further described by reference to the following non-limiting Figures and Examples.

Melanoma Diagnosis

Creation of Algorithm

Database Creation: Sample Preparation and microRNA Expression Profiling

To identify a panel of circulating microRNA suitable to diagnose an individual with melanoma, 0.5-2 ml of plasma was obtained from 36 individuals diagnosed with malignant melanoma and 12 normal controls (ie no melanoma). Details of the 48 individuals used in this study are provided in Table 4.

TABLE 4

Patient and specimen details for microRNA discovery set

| GeneSeq ID | Diagnosis | Type | Sex | Age | T | N | M | Stage |
|---|---|---|---|---|---|---|---|---|
| Mel48_001 | Melanoma | Fresh | F | 57 | T3b | N0 | M0 | IIB |
| Mel48_002 | Melanoma | Fresh | M | 35 | T4b | N0 | M0 | II |
| Mel48_003 | Melanoma | Fresh | F | 77 | T4b | N0 | M0 | II |
| Mel48_004 | Melanoma | Fresh | F | 76 | T1 | N0 | M0 | I |
| Mel48_005 | Melanoma | Fresh | F | 75 | T3 | N0 | M0 | IIB |
| Mel48_006 | Melanoma | Fresh | F | 74 | T2b | N0 | M0 | IIA |
| Mel48_007 | Melanoma | Fresh | F | 37 | T3 | N0 | M0 | IIB |
| Mel48_008 | Melanoma | Fresh | F | 52 | T4a | N0 | M0 | IIB |
| Mel48_017 | Melanoma | Fresh | F | 64 | T3a | N0 | M0 | IIA |
| Mel48_018 | Melanoma | Fresh | F | 88 | T0 | N1 | M0 | IV |
| Mel48_019 | Melanoma | Fresh | F | 71 | T3a | N0 | M0 | IIA |
| Mel48_020 | Melanoma | Fresh | F | 71 | T3a | N0 | M0 | IIA |
| Mel48_021 | Melanoma | Fresh | F | 37 | T3b | N0 | M0 | IIB |
| Mel48_022 | Melanoma | Fresh | F | 80 | T1b | N0 | M0 | IB |
| Mel48_023 | Melanoma | Fresh | M | 78 | T3d | N1a | M0 | IIIA |
| Mel48_024 | Melanoma | Fresh | M | 63 | T0 | N1 | M0 | IV |
| Mel48_025 | Melanoma | Archival | M | 57 | T2 | NO | MO0 | IIA |
| Mel48_026 | Melanoma | Archival | M | 35 | T2 | N0 | M0 | II |
| Mel48_027 | Melanoma | Archival | F | 77 | T4 | N0 | M0 | II |
| Mel48_028 | Melanoma | Archival | F | 76 | T4 | NI | M0 | II |
| Mel48_029 | Melanoma | Archival | M | 75 | T4 | N0 | M0 | III |
| Mel48_030 | Melanoma | Archival | F | 74 | T2 | N0 | M0 | II |
| Mel48_031 | Melanoma | Archival | M | 63 | T4 | N0 | M0 | IIB |
| Mel48_032 | Melanoma | Archival | F | 41 | TX | NX | M0 | IIB |
| Mel48_041 | Melanoma | Archival | F | 52 | T3a | NX | M0 | IIA |
| Mel48_042 | Melanoma | Archival | F | 50 | TX | N3 | M0 | IIIC |
| Mel48_043 | Melanoma | Archival | M | 51 | T2a | N0 | M0 | IB |
| Mel48_044 | Melanoma | Archival | F | 52 | T4b | NX | M1 | IV |
| Mel48_045 | Melanoma | Archival | M | 49 | T3b | NX | M0 | IIB |
| Mel48_046 | Melanoma | Archival | M | 40 | T1a | NX | M0 | IA |
| Mel48_047 | Melanoma | Archival | M | 65 | T4b | NX | M1b | IV |
| Mel48_048 | Melanoma | Archival | F | 74 | T4b | N3 | M0 | IIIC |
| Mel48_009 | Normal Donor | Fresh | F | 22 | | | | |
| Mel48_010 | Normal Donor | Fresh | F | 23 | | | | |

TABLE 4-continued

Patient and specimen details for microRNA discovery set

| GeneSeq ID | Diagnosis | Type | Sex | Age | T | N | M | Stage |
|---|---|---|---|---|---|---|---|---|
| Mel48_011 | Normal Donor | Fresh | F | 18 | | | | |
| Mel48_012 | Normal Donor | Fresh | F | 32 | | | | |
| Mel48_013 | Normal Donor | Fresh | F | 31 | | | | |
| Mel48_014 | Normal Donor | Fresh | F | 34 | | | | |
| Mel48_015 | Normal Donor | Fresh | F | 44 | | | | |
| Mel48_016 | Normal Donor | Fresh | F | 43 | | | | |
| Mel48_033 | Normal Donor | Archival | F | 19 | | | | |
| Mel48_034 | Normal Donor | Archival | M | 29 | | | | |
| Mel48_035 | Normal Donor | Archival | F | 24 | | | | |
| Mel48_036 | Normal Donor | Archival | M | 37 | | | | |
| Mel48_037 | Normal Donor | Archival | M | 49 | | | | |
| Mel48_038 | Normal Donor | Archival | M | 46 | | | | |
| Mel48_039 | Normal Donor | Archival | F | 47 | | | | |
| Mel48_040 | Normal Donor | Archival | F | 20 | | | | |

Cell-free microRNA purification was performed using the QIAGEN miRNeasy Serum/Plasma Kit (Cat No./ID: 217184), incorporating the miRNeasy Serum/Plasma Spike-In Control (Cat No./ID: 219610), as per manufacturer recommendations. RNA was eluted in 100 µl water and concentrated to 20 µl; 3 µl was used for profiling on the multiplexed nCounter platform from NanoString Technologies (Seattle, WA, USA).

The nCounter microRNA Assay detects 800 human microRNAs, curated from miRBase. RNA samples were prepared by ligating a specific DNA tag (miR-tag) onto the 3' end of each mature microRNA per the manufacturer's instructions. Excess tags were removed by restriction digestion at 37° C. Hybridizations were carried out by combining 5 µl of each microRNA-miR-Tag sample with 20 µl of nCounter Reporter probes in hybridization buffer and 5 µl of nCounter Capture probes (for a total reaction volume of 30 µl) at 65° C. for 16-20 h. Excess probes were removed using a two-step magnetic bead-based purification on the nCounter Prep Station.

Abundance of specific target molecules was quantified using the nCounter Digital Analyzer by counting the individual fluorescent barcodes and assessing target molecules. The data were collected using the nCounter Digital Analyzer after taking images of the immobilized fluorescent reporters in the sample cartridge using a CCD camera.

Data Processing and Normalisation

Raw Nanostring gene counts were adjusted for background noise by negative control adjustment. To control for variation in the amount of starting material present in each sample, data were then normalized to two spike-in probes; cel-miR-254 and osa-miR-414.

To prepare the data for statistical comparison between normal and melanoma classes, voom transformation was then applied. This method estimates the mean-variance relationship of the log-counts, generates a precision weight for each observation and enters these into the limma empirical Bayes analysis pipeline for downstream gene selection.

The empirical Bayes method of gene expression analysis is similar to reduction of the estimated sample variances towards a pooled estimate. This results in far more stable assessment of expression level variance between and within classes, particularly when the number of samples measurements is small, relative to the number of genes analyzed in each.

MicroRNA Signature 1 Development: Melanoma vs Normal Controls

Gene expression profiles of melanoma patient plasma and normal control plasma were compared using voom+limma analysis (Law C W, Chen Y, Shi W, Smyth G K: voom: Precision weights unlock linear model analysis tools for RNA-seq read counts. Genome Biol 2014, 15(2):R29). All genes with a minimum count per million (CPM) of 15 in at least 5 samples were evaluated. This approach has been demonstrated to result in the most accurate method to detect true differential expression, with the lowest FDR, compared to other techniques for comparing gene expression profiles, including the t-test.

Fold change, p-value and false discovery rate (FDR) for each gene in the normalised microRNA plasma dataset were calculated. Those genes with an FDR of <0.01 and a fold-change >2.0 were identified (n=38). FIG. 1 shows the relationship between FDR and fold change (LUG FC) for each gene before and after filtering. The 38 gene set is referred to as MEL38 (Table 5).

TABLE 5

Gene signature 1 (MEL38) with fold change and details of the statistical significance between plasma from individuals with or without melanoma.

| MicroRNA ID | MicroRNA Accession | Log mean fold-change (Melanoma/Normal) | FDR | P-value | Adjusted P-val |
|---|---|---|---|---|---|
| hsa-miR-424-5p | MIMAT0001341 | 2.65 | 4.30E−15 | 5.93E−18 | 4.30E−15 |
| hsa-miR-301a-3p | MIMAT0000688 | 2.28 | 5.50E−05 | 1.52E−06 | 5.50E−05 |
| hsa-miR-299-3p | MIMAT0000687 | 1.95 | 1.77E−08 | 1.22E−10 | 1.77E−08 |
| hsa-miR-181b-5p | MIMAT0000257 | 1.60 | 9.01E−06 | 1.64E−07 | 9.01E−06 |
| hsa-miR-337-5p | MIMAT0004695 | 1.58 | 5.24E−03 | 5.22E−04 | 5.24E−03 |
| hsa-miR-34a-5p | MIMAT0000255 | 1.53 | 8.87E−09 | 3.67E−11 | 8.87E−09 |

TABLE 5-continued

Gene signature 1 (MEL38) with fold change and details of the statistical
significance between plasma from individuals with or without melanoma.

| MicroRNA ID | MicroRNA Accession | Log mean fold-change (Melanoma/Normal) | FDR | P-value | Adjusted P-val |
|---|---|---|---|---|---|
| hsa-miR-454-3p | MIMAT0003885 | 1.52 | 3.07E−04 | 1.07E−05 | 3.07E−04 |
| hsa-miR-431-5p | MIMAT0001625 | 1.52 | 3.24E−03 | 2.86E−04 | 3.24E−03 |
| hsa-miR-4532 | MIMAT0019071 | 1.50 | 3.47E−04 | 1.45E−05 | 3.47E−04 |
| hsa-miR-1910-5p | MIMAT0007884 | 1.47 | 9.01E−06 | 1.74E−07 | 9.01E−06 |
| hsa-miR-27a-3p | MIMAT0000084 | 1.42 | 5.50E−03 | 5.68E−04 | 5.50E−03 |
| hsa-miR-497-5p | MIMAT0002820 | 1.34 | 1.05E−08 | 5.80E−11 | 1.05E−08 |
| hsa-miR-548a-5p | MIMAT0004803 | 1.26 | 3.07E−04 | 1.10E−05 | 3.07E−04 |
| hsa-miR-152-3p | MIMAT0000438 | 1.25 | 5.74E−06 | 9.48E−08 | 5.74E−06 |
| hsa-miR-1537-3p | MIMAT0007399 | 1.20 | 3.47E−04 | 1.48E−05 | 3.47E−04 |
| hsa-miR-1258 | MIMAT0005909 | 1.19 | 7.28E−04 | 3.99E−05 | 7.28E−04 |
| hsa-miR-154-5p | MIMAT0000452 | 1.14 | 5.83E−03 | 6.27E−04 | 5.83E−03 |
| hsa-miR-450a-5p | MIMAT0001545 | 1.11 | 3.94E−03 | 3.64E−04 | 3.94E−03 |
| hsa-miR-2682-5p | MIMAT0013517 | 1.08 | 5.16E−03 | 5.04E−04 | 5.16E−03 |
| hsa-miR-548ad-3p | MIMAT0018946 | −1.01 | 3.07E−04 | 1.19E−05 | 3.07E−04 |
| hsa-miR-219a-2-3p | MIMAT0004675 | −1.03 | 2.99E−03 | 2.59E−04 | 2.99E−03 |
| hsa-miR-4787-3p | MIMAT0019957 | −1.04 | 5.82E−03 | 6.18E−04 | 5.82E−03 |
| hsa-miR-520d-3p | MIMAT0002856 | −1.04 | 2.42E−04 | 7.65E−06 | 2.42E−04 |
| hsa-miR-522-3p | MIMAT0002868 | −1.05 | 7.53E−04 | 4.36E−05 | 7.53E−04 |
| hsa-miR-1269a | MIMAT0005923 | −1.06 | 1.12E−06 | 1.08E−08 | 1.12E−06 |
| hsa-miR-205-5p | MIMAT0000266 | −1.09 | 1.90E−07 | 1.57E−09 | 1.90E−07 |
| hsa-miR-553 | MIMAT0003216 | −1.10 | 4.27E−04 | 1.94E−05 | 4.27E−04 |
| hsa-miR-3131 | MIMAT0014996 | −1.24 | 9.06E−06 | 1.95E−07 | 9.06E−06 |
| hsa-miR-1264 | MIMAT0005791 | −1.25 | 1.05E−03 | 7.11E−05 | 1.05E−03 |
| hsa-miR-764 | MIMAT0010367 | −1.27 | 5.15E−05 | 2.48E−06 | 5.15E−05 |
| hsa-miR-3928-3p | MIMAT0018205 | −1.45 | 9.06E−06 | 2.00E−07 | 9.06E−06 |
| hsa-miR-548l | MIMAT0005889 | −1.51 | 4.65E−09 | 1.28E−11 | 4.65E−09 |
| hsa-miR-138-5p | MIMAT0000430 | −1.51 | 4.70E−06 | 6.48E−08 | 4.70E−06 |
| hsa-miR-1973 | MIMAT0009448 | −1.55 | 1.30E−04 | 3.77E−06 | 1.30E−04 |
| hsa-miR-624-3p | MIMAT0004807 | −1.57 | 4.23E−06 | 5.25E−08 | 4.23E−06 |
| hsa-miR-1306-5p | MIMAT0022726 | −1.58 | 2.34E−03 | 1.90E−04 | 2.34E−03 |
| hsa-miR-1-5p | MIMAT0031892 | −1.63 | 4.79E−06 | 7.26E−08 | 4.79E−06 |
| hsa-miR-1302 | MIMAT0005890 | −1.73 | 7.28E−04 | 4.03E−05 | 7.28E−04 |

Use of the MEL38 Gene Signature and Plasma microRNA Database to Train a Classification Algorithm In order to demonstrate the use of the MEL38 gene signature in classifying samples as melanoma or normal, a support vector machine (SVM) algorithm was trained using the 46 samples from the database which passed quality control.

The prediction rule is defined by the inner sum of the weights ($w_i$) shown in Table 6 and expression ($x_i$) of significant genes. The expression is the log intensities for voom-normalized Nanostring gene expression data. A sample is classified to the class Melanoma if the sum is greater than the threshold; that is, $\Sigma_i w_i x_i$>threshold. The threshold for the Support Vector Machine predictor is 11. This threshold may vary depending on the desired sensitivity and specificity of the result.

FIG. 2 shows the 38-gene SVM scores for each samples in the 48-MEL38 discovery database. Scores >11 correspond to a melanoma result. FIG. 3 shows the MEL38 SVM scores for samples in the training series, grouped by melanoma status and melanoma stage (I-IV).

TABLE 6

SVM weights generated from cross validation of
the 48-sample melanoma plasma microRNA database

| MicroRNA | Support Vector Machine Weight |
|---|---|
| hsa-miR-424-5p | 0.1801 |
| hsa-miR-34a-5p | 0.2831 |
| hsa-miR-764 | −0.132 |
| hsa-miR-3928-3p | 0.1564 |
| hsa-miR-497-5p | −0.1439 |
| hsa-miR-624-3p | 0.198 |
| hsa-miR-548a-5p | 0.22 |
| hsa-miR-1306-5p | −0.1834 |
| hsa-miR-520d-3p | 0.195 |
| hsa-miR-4787-3p | 0.3574 |
| hsa-miR-548l | −0.2426 |
| hsa-miR-181b-5p+ | 0.307 |
| hsa-miR-1258 | 0.0516 |
| hsa-miR-1910-5p | 0.3589 |
| hsa-miR-1264 | −0.5976 |
| hsa-miR-1269a | 0.0922 |
| hsa-miR-1973 | −0.1673 |
| hsa-miR-154-5p | 0.3582 |
| hsa-miR-152-3p | 0.2877 |
| hsa-miR-553 | −0.1174 |
| hsa-miR-205-5p | −0.1746 |
| hsa-miR-3131 | −0.1399 |
| hsa-miR-299-3p | 0.2438 |
| hsa-miR-2682-5p | 0.5138 |
| hsa-miR-454-3p | 0.2297 |
| hsa-miR-1-5p | −0.0207 |
| hsa-miR-1537-3p | −0.0459 |
| hsa-miR-138-5p | 0.0691 |
| hsa-miR-431-5p | 0.0467 |

TABLE 6-continued

SVM weights generated from cross validation of the 48-sample melanoma plasma microRNA database

| MicroRNA | Support Vector Machine Weight |
|---|---|
| hsa-miR-450a-5p | −0.4791 |
| hsa-miR-548ad-3p | 0.0699 |
| hsa-miR-4532 | 0.2684 |
| hsa-miR-301a-3p | −0.3307 |
| hsa-miR-337-5p | −0.1254 |
| hsa-miR-522-3p | 0.5152 |
| hsa-miR-219a-2-3p | 0.5351 |
| hsa-miR-27a-3p | 0.1954 |
| hsa-miR-1302 | −0.1477 |

The MEL38 gene set can also be used with a nearest-centroid algorithm, in which the MEL38 gene expression data from a new sample is correlated against a melanoma and normal 'template' or centroid. The centroid to which the new sample has the highest correlation is the result. The centroid data is shown in Table 7.

TABLE 7

MEL38 nearest centroid algorithm.

| Gene ID | Melanoma Centroid | Normal Centroid |
|---|---|---|
| hsa-miR-424-5p | 5.1023 | 4.1817 |
| hsa-miR-34a-5p | 4.9068 | 4.2929 |
| hsa-miR-764 | 4.6969 | 4.2322 |
| hsa-miR-3928-3p | 5.3653 | 5.0888 |
| hsa-miR-497-5p | 4.9612 | 4.3228 |
| hsa-miR-624-3p | 4.0397 | 3.8785 |
| hsa-miR-548a-5p | 5.8282 | 5.0157 |
| hsa-miR-1306-5p | 4.3106 | 4.2768 |
| hsa-miR-520d-3p | 4.5938 | 4.5103 |
| hsa-miR-4787-3p | 4.3386 | 3.9356 |
| hsa-miR-548l | 4.1429 | 4.0171 |
| hsa-miR-181b-5p | 4.9169 | 4.2222 |
| hsa-miR-1258 | 6.2072 | 5.0175 |
| hsa-miR-1910-5p | 4.9434 | 3.9646 |
| hsa-miR-1264 | 4.3201 | 4.8185 |
| hsa-miR-1269a | 4.5979 | 4.4874 |
| hsa-miR-1973 | 4.0559 | 4.3078 |
| hsa-miR-154-5p | 3.8682 | 3.4823 |
| hsa-miR-152-3p | 3.8433 | 3.3995 |
| hsa-miR-553 | 5.2667 | 5.3566 |
| hsa-miR-205-5p | 4.1302 | 4.3071 |
| hsa-miR-3131 | 5.4539 | 5.0833 |
| hsa-miR-299-3p | 4.5868 | 3.9978 |
| hsa-miR-2682-5p | 3.8625 | 3.5163 |
| hsa-miR-454-3p | 4.0446 | 3.5372 |
| hsa-miR-1-5p | 4.1107 | 4.1421 |
| hsa-miR-1537-3p | 4.0141 | 3.9776 |
| hsa-miR-138-5p | 4.0966 | 4.0876 |
| hsa-miR-431-5p | 3.8406 | 3.5352 |
| hsa-miR-450a-5p | 4.1058 | 4.2231 |
| hsa-miR-548ad-3p | 5.3252 | 4.786 |
| hsa-miR-4532 | 4.5461 | 3.7734 |
| hsa-miR-301a-3p | 4.8278 | 4.3873 |
| hsa-miR-337-5p | 4.2135 | 4.1874 |
| hsa-miR-522-3p | 4.8246 | 4.6588 |
| hsa-miR-219a-2-3p | 4.3896 | 3.8757 |
| hsa-miR-27a-3p | 4.1169 | 3.9092 |
| hsa-miR-1302 | 3.8279 | 4.2981 |

Another type of algorithm is the Compound Covariate Predictor. The prediction rule is defined by the inner sum of the weights ($w_i$) shown in Table 8 and expression ($x_i$) of significant genes. The expression is the log intensities for voom-normalized Nanostring gene expression data. A sample is classified to the class Melanoma if the sum is greater than the threshold; that is, $\Sigma_i w_i x_i >$ threshold. The threshold for the Compound Covariate predictor is 137.059

TABLE 8

Compound Covariate Predictor gene weights

| Gene ID | Compound Covariate Predictor weight |
|---|---|
| hsa-miR-424-5p | 2.2478 |
| hsa-miR-34a-5p | 1.5872 |
| hsa-miR-764 | 1.1235 |
| hsa-miR-3928-3p | 0.5694 |
| hsa-miR-497-5p | 1.4889 |
| hsa-miR-624-3p | 0.5242 |
| hsa-miR-548a-5p | 1.8694 |
| hsa-miR-1306-5p | 0.0866 |
| hsa-miR-520d-3p | 0.231 |
| hsa-miR-4787-3p | 1.2083 |
| hsa-miR-548l | 0.4308 |
| hsa-miR-181b-5p | 1.8521 |
| hsa-miR-1258 | 2.6081 |
| hsa-miR-1910-5p | 2.2403 |
| hsa-miR-1264 | −1.2896 |
| hsa-miR-1269a | 0.2832 |
| hsa-miR-1973 | −0.795 |
| hsa-miR-154-5p | 1.6764 |
| hsa-miR-152-3p | 2.2561 |
| hsa-miR-553 | −0.1838 |
| hsa-miR-205-5p | −0.4945 |
| hsa-miR-3131 | 0.8258 |
| hsa-miR-299-3p | 1.5227 |
| hsa-miR-2682-5p | 1.4378 |
| hsa-miR-454-3p | 1.7223 |
| hsa-miR-1-5p | −0.0982 |
| hsa-miR-1537-3p | 0.1062 |
| hsa-miR-138-5p | 0.0271 |
| hsa-miR-431-5p | 1.0752 |
| hsa-miR-450a-5p | −0.3627 |
| hsa-miR-548ad-3p | 1.2046 |
| hsa-miR-4532 | 1.9668 |
| hsa-miR-301a-3p | 0.935 |
| hsa-miR-337-5p | 0.0764 |
| hsa-miR-522-3p | 0.3791 |
| hsa-miR-219a-2-3p | 1.2588 |
| hsa-miR-27a-3p | 0.6529 |
| hsa-miR-1302 | −1.5295 |

Other supervising learning model are envisaged including training a feed forward neural network. In contrast to the SVM described above where a hyperplane is fitted between the two classes: melanoma or not melanoma, the neural network may require more training data in order to generate a multi-layer fully-connected backpropagation model. The trained neural network can be optimised by pruning unactivated parts of the neural network or by fusing multiple layers of the neural network into a single computational step. For inferencing, the properly weighted neural network is provided with unseen data of biological samples and classifies whether the unseen biological sample has a higher probability belonging to the melanoma class or the not melanoma class.

Validation of Melanoma Diagnostic microRNA Signature (MEL38)

To validate the diagnostic significance of the circulating microRNAs identified from the discovery series of 48 individuals, additional genomic datasets were obtained from the publicly available data repository NCBI GEO (ncbi.nlm.nih.gov/geo) by searching for the phrases 'melanoma' and 'microRNA'.

Validation 1: Peripheral Blood from Individuals with or without Melanoma

As no other group has published a multi-sample plasma-based microRNA profiling study to date, it was not possible to find a validation cohort that matched the exact composition of the discovery series generated for this application. The most suitable validation dataset found was accession GSE20994, which represents peripheral blood microRNA profiles of melanoma patients (n=35) and normal controls (n=22). Data were generated using a custom microRNA oligonucleotide microarray, based on release 13.0 of the Sanger MirBase; (febit Homo Sapiens miRBase 13.0, Hummingbird Diagnostics, Heidelberg, Germany. NCBI GEO Platform ID GPL9040).

By comparing exact microRNA sequences between the Nanostring nCounter human microRNA codesets and the febit Homo sapiens miRBASE 13.0 platforms, 28 of the 38 genes in MEL38 were matched to the peripheral blood validation dataset. Principal component analysis was used to visualize the difference between normal and melanoma samples, which is shown in FIG. 6 (squares=normal, spheres=melanoma)

To determine the ability of these microRNAs to stratify individuals with or without melanoma, three cross-validated classification models were tested, without additional feature selection or modification to the gene list. The classification algorithms tested were nearest centroid classification, compound covariate prediction and support vector machine classification. Results of this analysis are show in Tables 9-11.

Receiver operator curve analysis was performed on the cross-validated, partially-retrained, SVM classifications, resulting in an AUC of AUC=0.96 (FIG. 4).

An additional sample permutation analysis was performed to determine the overall significance of the result. Based on 100 permutations, the probability of observing the classification accuracy shown in Table 7 by chance alone is P<0.01.

TABLE 9

Performance of the Nearest Centroid Classifier for melanoma vs normal control using 28/38 microRNAs from MEL38 matched to independent validation series.

| Class | Sensitivity | Specificity | PPV | NPV |
|---|---|---|---|---|
| Melanoma | 0.943 | 0.818 | 0.892 | 0.9 |
| Normal | 0.818 | 0.943 | 0.9 | 0.892 |

TABLE 10

Performance of the Compound Covariate Predictor for melanoma vs normal control using 28/38 microRNAs from MEL38 matched to independent validation series.

| Class | Sensitivity | Specificity | PPV | NPV |
|---|---|---|---|---|
| Melanoma | 0.943 | 0.818 | 0.892 | 0.9 |
| Normal | 0.818 | 0.943 | 0.9 | 0.892 |

TABLE 11

Performance of the Support Vector Machine classifier for melanoma vs normal control using 28/38 microRNAs from MEL38 matched to independent validation series (partial cross validation used).

| Class | Sensitivity | Specificity | PPV | NPV |
|---|---|---|---|---|
| Melanoma | 0.886 | 0.864 | 0.912 | 0.826 |
| Normal | 0.864 | 0.886 | 0.826 | 0.912 |

The 28/38-gene SVM model was then applied to the validation series data using the SVM weights obtained from the discovery series analysis (Table 6) without additional partial re-training or gene selection. The results of this method of classifier testing is shown in FIG. 5 and Table 12.

The AUC of this method was 0.794 (P<0.0001) and the optimal classification threshold for the 28-gene subset model was determined to be >9.25. This gave a sensitivity of 71% (95% CI: 53.7-85.4) and specificity of 86% (95% CI: 65.1-97.1).

Other classification thresholds and associated performance data were calculated and are shown in Table 12, demonstrating the impact of adjusting the classification threshold of a multi-gene diagnostic score on the sensitivity or specificity of the predictions made.

TABLE 12

28/38-gene SVM classification thresholds and associated validation series performance results. Results greater than the threshold = prediction of melanoma.

| Classification threshold | Sensitivity | 95% CI | Specificity | 95% CI |
|---|---|---|---|---|
| ≥4.9 | 100.00 | 90.0-100.0 | 0.00 | 0.0-15.4 |
| >6.19 | 91.43 | 76.9-98.2 | 0.00 | 0.0-15.4 |
| >6.54 | 91.43 | 76.9-98.2 | 18.18 | 5.2-40.3 |
| >6.63 | 88.57 | 73.3-96.8 | 18.18 | 5.2-40.3 |
| >7.18 | 88.57 | 73.3-96.8 | 45.45 | 24.4-67.8 |
| >7.19 | 85.71 | 69.7-95.2 | 45.45 | 24.4-67.8 |
| >8.04 | 85.71 | 69.7-95.2 | 54.55 | 32.2-75.6 |
| >8.1 | 82.86 | 66.4-93.4 | 54.55 | 32.2-75.6 |
| >8.2 | 82.86 | 66.4-93.4 | 59.09 | 36.4-79.3 |
| >8.37 | 77.14 | 59.9-89.6 | 59.09 | 36.4-79.3 |
| >8.58 | 77.14 | 59.9-89.6 | 68.18 | 45.1-86.1 |
| >8.65 | 74.29 | 56.7-87.5 | 72.73 | 49.8-89.3 |
| >8.9 | 74.29 | 56.7-87.5 | 77.27 | 54.6-92.2 |
| >9.09 | 71.43 | 53.7-85.4 | 77.27 | 54.6-92.2 |
| >9.25 | 71.43 | 53.7-85.4 | 86.36 | 65.1-97.1 |
| >9.67 | 60.00 | 42.1-76.1 | 86.36 | 65.1-97.1 |
| >9.72 | 60.00 | 42.1-76.1 | 90.91 | 70.8-98.9 |
| >9.73 | 57.14 | 39.4-73.7 | 90.91 | 70.8-98.9 |
| >9.81 | 57.14 | 39.4-73.7 | 95.45 | 77.2-99.9 |
| >10.98 | 31.43 | 16.9-49.3 | 95.45 | 77.2-99.9 |
| >11.03 | 31.43 | 16.9-49.3 | 100.00 | 84.6-100.0 |
| >14.15 | 0.00 | 0.0-10.0 | 100.00 | 84.6-100.0 |

Statistical analyses of the circulating microRNA signatures for individuals in the training and independent validation series was performed using general linear models (Table 13). The SVM score for individuals in the training series showed a highly significant difference between melanoma and normal samples (P<0.001), and no association with age or gender. These results were mirrored in the independent validation series, where the association with disease stage was P<0.001 and P=0.002 with or without partial retraining of the signature.

In the melanoma-patient only subset of both series, tumour thickness, melanoma type (superficial, nodal or amelanotic), disease stage (I-IV), age and sex (where available) were then investigated for their association with the SVM classification score. None of the variables tested were found to be statistically significant in any of the general linear models tested.

These data show that the multi-gene classification score developed in this study is significantly associated with disease state (ie the presence or absence of melanoma), independent of age, gender or tumour characteristics such as thickness, subtype or stage).

TABLE 13

General linear model analysis of MEL28/38 gene signature vs clinicopathological variables

| Gene signature vs. | Training Series (n = 48) | Independent Validation Series (n = 57) | |
| --- | --- | --- | --- |
| | | Without SVM re-training | With partial SVM re-training |
| GLM 1: All individuals: | | | |
| Disease state (melanoma vs normal) | <0.001 | 0.002 | <0.001 |
| Age | 0.826 | 0.612 | 0.426 |
| Sex | 0.239 | 0.976 | 0.884 |
| GLM 2: Melanoma patients only: | | | |
| Age | 0.894 | 0.505 | 0.420 |
| Sex | 0.93 | 0.487 | 0.824 |
| Melanoma thickness | 0.634 | 0.809 | 0.364 |
| Melanoma type | N/A | 0.693 | 0.252 |
| Stage I-V | 0.928 | 0.242 | 0.561 |

In summary, a 22-gene subset of the MEL38 microRNA gene signature is able to stratify an independent series of individuals with or without melanoma with a sensitivity of 71-97% (depending on how the model is applied) and specificity of 86%.

Several important caveats to these results are (i) the classifier is based on a subset of the total signature due to the older version of mirBase used (ii) the genes were measured using microarray rather than Nanostring or other digital method and, (ii) the specimen type was whole peripheral blood rather than plasma. These differences in methodology compared to those used for the discovery series represent a 'stress-testing' of the gene signature and classification method.

Assessment of Minimum Subset of MEL38 Required for Diagnostic Classification

To determine the minimum set of genes required to classify a sample as either normal or melanoma, PAM analysis was performed (Tibshirani, 2002, Diagnosis of multiple cancer types by shrunken centroids of gene expression). This method evaluates different subsets of a gene signature and reports the cross validated performance of each sub-signature and is similar in nature to the nearest centroid classifier (Table 7).

Applied to the training series of 48 individuals, a subset of 16 of the 38 genes was required to achieve significant classification accuracy over random chance (ie >50% accuracy). These 16 genes are: hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p.

To verify this analysis, the same PAM analysis process was performed on the independent validation series of whole-blood microRNA profiles starting with the 28 genes from the MEL38 signature present in the validation series analysed above. Beginning with 28 genes, 89% of cases are correctly classified as melanoma or normal. As the number of genes used gets smaller, the classification error increases, with n=4 genes resulting in a greater than 50% misclassification rate. Therefore a set of at least 4 genes is required to generate a classification result with greater accuracy than random chance.

The minimum set of 4 microRNAs are: hsa-miR-181b-5p, hsa-miR-34a-5p, hsa-miR-497-5p and hsa-miR-431-5p. Three of these 4 genes overlap with the minimum 16 set identified from the training series PAM analysis. As such, the combined minimum set of genes required for diagnosis of melanoma using circulating microRNAs is the following MEL17:

hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p and hsa-miR-431-5p.

Figure 7:
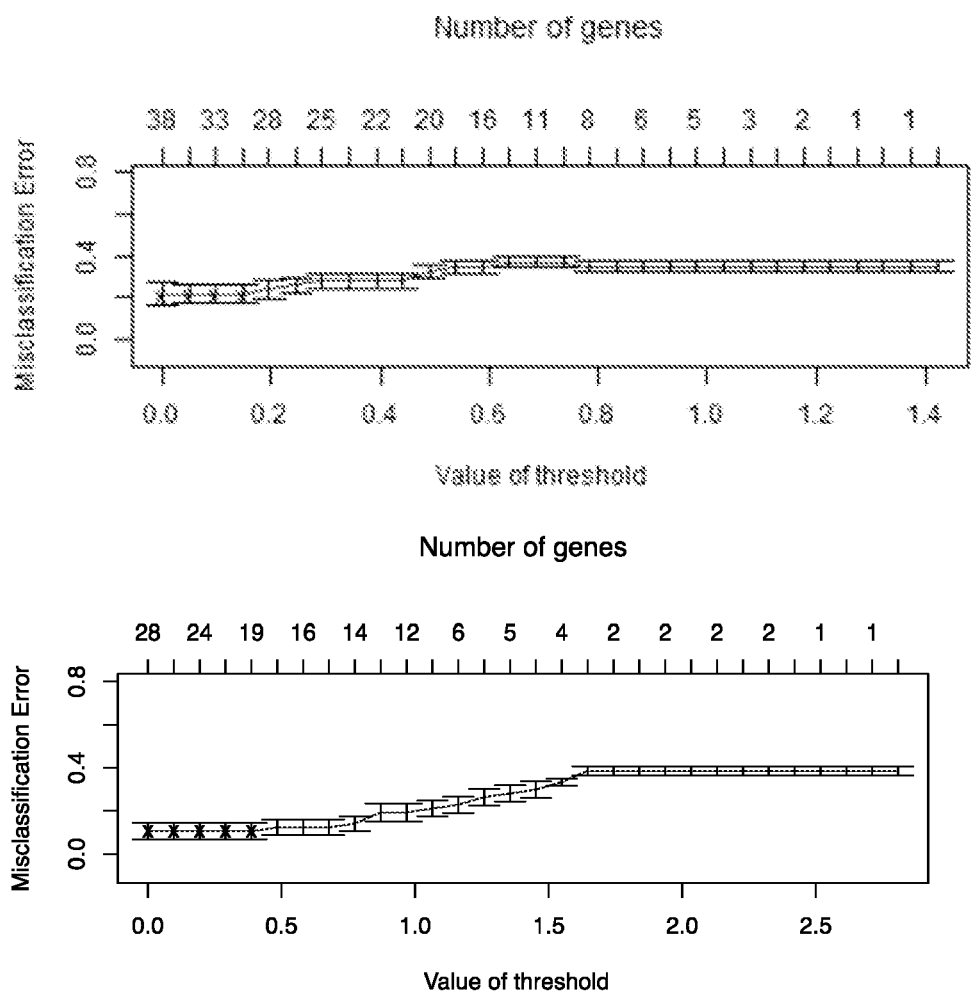

FIG. 7 illustrates the cross validation PAM results of the training and validation series used to identify the minimum set of 18 combined genes. These graphs display the gene number along the x-axis and the corresponding classification accuracy on the y-axis.

Validation 2: Melanoma Cell Line, Normal Skin Cell Line and Exosomes Isolated from Each As an additional in-vitro validation of the MEL38 gene signature, an Affymetrix microlRNA GeneChip dataset (GEO ID: GSE35387) was analysed. This study profiled the microRNA expression profiles of normal melanocytes, melanoma cells and their exosomes. Exosomes are small membraneous vesicles secreted into body fluids by tumors. Tumor exosomes contain intact and functional mRNAs, small RNAs (including miRNAs), and proteins that can alter the cellular environment to favor tumor growth.

By comparing the expression levels of the genes in MEL38 between melanoma cells, melanoma exosomes, normal melanocytes and normal exosomes, it is possible to infer the origin of the circulating microRNAs present in the MEL38 signature. By matching microRNA probes between Nanostring and Affymetrix platforms using gene sequences, 26 of 38 genes were identified. A cross validated SVM model showed 100% separation of melanoma (cells or exosomes) from normal (cells vs exosomes) profiles (FIG. 9). In addition, hierarchical clustering of the 26-gene dataset showed robust stratification of melanoma cells/exosomes from normal melanocyte cells and exosomes (FIG. 8).

Validation 3: MicroRNA Expression in Melanoma Tissue and Benign Nevus Biopsies

As another way to examine the origin of the circulating microRNAs detected in this study, a previously published dataset of microRNA profiles generated from formalin-fixed, paraffin-embedded melanoma (n=16) and melanocytic nevi (n=3) samples was downloaded from EBI ArrayExpress (accession E-MTAB-4915).

Thirteen of the MEL38 genes were differentially expressed between disease status (P<0.05) and 21 had fold-change difference of 1>1.51. Hierarchical clustering using all 38 genes (MEL38) measured in melanoma and nerves FFPE tissue showed separation of samples based on disease status as shown in FIG. 10. In addition, a cross-validated SVM using all 38 genes was able to perfectly separate the melanoma profiles from the nevi, confirming the disease-state significance of the gene signature. FIG. 11 shows the MEL38 SVM scores for this dataset.

Validation 4: MicroRNA Expression in Melanoma Tissue and Benign Nevus Biopsies

To explore the ability of the Melaseq MEL38 signature to function as biomarker to aid in the histological diagnosis of melanoma, dataset GSE35579 was downloaded from the NCBI Gene Expression Omnibus. This dataset was generated by the Melton Lab at the University of Edinburgh, using a customised version of the Illumina microRNA beadchip (NCBI platform ID: GPL15183)[8].

As stated in the dataset description, total RNA was obtained from 61 FFPE samples comprised of 11 benign naevi, 20 primary melanoma and 21 metastatic melanoma biopsies. The microRNA platform used contained 735 targets, which included 470 well-annotated human microRNAs. Target matching to MEL38 was performed using target annotation files and individual probe sequences. Twenty seven of the 38 microRNAs were identified from this process (71%).

The ability of this subset of MEL38 to differentiate between the specimen types present in this dataset was explored by partial retraining of the support vector machine (SVM) algorithm, using the binary classes of benign vs melanoma (primary and metastatic). This involves training the SVM algorithm on the data present, using cross validation, but without additional gene selection or filtering. The classification accuracy observed was 94-96%, depending on the cross validation method (leave one out, 10-fold or 0.632+bootstrap). Sensitivity and specificity for prediction of melanoma status was 0.97 and 0.85 respectively. The classifiers positive predictive value was 0.96 and its negative predictive value was 0.89.

A p-value for the global test of the hypothesis that the predictor is picking up the random noise in the data by a separate permutation step in which class labels were permuted 100 times. For each permutation samples are classified, and the cross-validated misclassification rate of each classifier is computed as a proportion of correctly predicted samples. The global significance of the 27-microRNA subset classifier is P<0.01.

To visualise the results of the partially re-trained classifier, the final 27-microRNA SVM was applied to the dataset by taking the sum of weighted microRNA abundance measurements, resulting in per-sample classification scores. These scores are shown in FIG. 12.

The mean classification score for the benign nevus class was 3.3, compared to 6.7 for the combined primary and metastatic melanoma class. Within the melanoma category, metastatic tumours had a mean classification score of 7.3, compared to 5.4 for the primary melanomas, despite the classifier being trained to detect them as one class. A t-test of difference in primary vs metastatic tumour classification scores showed the result to be statistically significant (P=2.03×10$^{-5}$)

These data show that even when only a 27-gene subset of Me138 is available, it is still possibly to differentiate benign naevi from melanoma. They also reveal that metastatic melanoma samples have a significantly higher (ie more melanoma-like) microRNA profile.

Summary of microRNA Signature 1 (MEL38) Development and Validation

A novel series of 38 circulating microRNAs was discovered by comparing Nanostring nCounter profiles generated from 48 plasma samples from individuals with and without cutaneous melanoma. In the discovery series (database), these genes were differentially expressed between normal control and melanoma patient plasma with a 2-fold or greater difference and a statistical significance of P<0.005. These selection criteria correspond to a less than 1 in 100 chance of false discovery for each gene.

The diagnostic ability of the 38 gene signature was evaluated in an independent series of microRNA profiles, not used in the gene selection or algorithm training process. These data were generated from peripheral blood taken from a series of 51 individuals, again with or without melanoma. Cross validated classification using the subset of the 38 gene set available showed a high degree of separation; 97% sensitivity and 86% specificity. Without partial-retraining of the signature, the sensitivity was 79%.

To explore the potential origin of the microRNAs in the 38-gene signature, an analysis of microRNA profiles of melanoma cells, normal melanocytes and experimentally derived exosomes was performed. Clustering of the data showed distinct separation of normal melanocyte from melanoma cell profiles, with similarity in expression patterns between cells and exosomes of each. This suggests that the microRNAs detected in the blood of individuals with melanoma which comprise the MEL38 signature have originated from melanoma or normal melanocyte cells.

Finally, the genes in the MEL38 signature were compared between tissue biopsies of malignant melanoma and benign nevi. Hierarchical clustering of samples using the 38 genes showed separation of melanoma from nevi, again supporting the hypothesis that the microRNAs identified in this study exhibit different levels between disease states and are therefore valid diagnostic markers.

Creating a miRNA Expression Staging Score

MicroRNA Signature 2 Development: Identifying Circulating microRNAs with Expression Levels Correlated to the Clinical Stage of Malignant Melanoma (I to IV)

To identify specific plasma microRNAs with patterns of expression that correlate with the stage of melanoma, plasma profiles from individuals with melanoma were grouped into stage I, II, III and IV (refer Table 8). Voom+ limma analysis was performed on all genes that passed the minimum detection threshold to identify those with significant differences between any pair of stages (ie. 1 vs 2, 2 vs 3, 3 vs 4, 1 vs 3, 2 vs 4). Significance was defined as FDR<0.1 and fold-change in expression of 2 or greater. This identified a set of 37 candidate genes for further evaluation.

Next, to identify genes with linear pattern of up or down regulation with tumour stage, the per-stage mean expression of each gene, relative to stage I, was correlated with stage. Genes with a correlation coefficient <−0.7 or >0.7 were selected for further analysis. Eight genes already present in signature 1 (MEL38), plus the top 5 positively and top 5 negatively correlated genes were chosen, giving a total melanoma staging signature of 18 genes (Table 14). The average fold change of each gene relative to their expression in stage I is shown in FIG. 13.

With all or a subset of these 18 genes, it is possible to identify the stage of melanoma in a patient previously diagnosed with the disease, either using the MEL38 gene signature or by conventional methods. A minimum of 2 genes would be required for accurate staging, including one positively and one negatively correlated gene, eg hsa-miR-199b-5p (correlation coefficient: −0.98; ie expression decreases as stage increases) and hsa-miR-3127-5p (correlation: 0.95; ie. Expression increases as stage increases).

TABLE 14

Plasma microRNAs with patterns of gene expression correlated with melanoma stage I-IV ("MEL18").

| MicroRNA ID | Stage 1 | Stage 2 | Stage 3 | Stage 4 | Correlation | FDR |
|---|---|---|---|---|---|---|
| hsa-miR-199b-5p | 0.00 | −1.33 | −2.04 | −2.62 | −0.980 | 2.52E−03 |
| hsa-miR-660-5p | 0.00 | −1.05 | −2.24 | −2.24 | −0.946 | 2.86E−03 |
| hsa-miR-337-5p | 0.00 | −1.11 | −3.16 | −3.02 | −0.936 | 8.79E−06 |
| hsa-let-7e-5p | 0.00 | −1.11 | −3.15 | −2.90 | −0.925 | 2.40E−05 |
| hsa-miR-652-3p | 0.00 | −1.91 | −3.95 | −3.69 | −0.924 | 5.57E−04 |
| hsa-miR-331-3p | 0.00 | −1.60 | −3.41 | −3.08 | −0.914 | 6.44E−03 |
| hsa-miR-1537-3p | 0.00 | −1.06 | −2.39 | −2.12 | −0.909 | 2.08E−03 |
| hsa-miR-301a-3p | 0.00 | −0.37 | −3.27 | −2.91 | −0.888 | 2.93E−03 |
| hsa-miR-27a-3p | 0.00 | −1.23 | −3.32 | −2.55 | −0.859 | 9.70E−04 |
| hsa-miR-154-5p | 0.00 | −3.20 | −3.82 | −3.77 | −0.846 | 8.79E−06 |
| hsa-miR-299-3p | 0.00 | −0.99 | −2.89 | −1.92 | −0.798 | 2.61E−03 |
| hsa-miR-152-3p | 0.00 | −1.45 | −2.38 | −1.55 | −0.726 | 2.86E−03 |
| hsa-miR-105-5p | 0.00 | 0.01 | −0.22 | 1.79 | 0.710 | 6.94E−03 |
| hsa-miR-127-5p | 0.00 | −0.37 | 1.43 | 1.06 | 0.752 | 9.70E−04 |
| hsa-miR-521 | 0.00 | 0.18 | 0.26 | 1.77 | 0.850 | 3.39E−03 |
| hsa-miR-4787-3p | 0.00 | 0.07 | 0.49 | 1.64 | 0.909 | 6.29E−03 |
| hsa-miR-1180-3p | 0.00 | 0.03 | 0.72 | 1.62 | 0.941 | 5.58E−03 |
| hsa-miR-3127-5p | 0.00 | 0.59 | 0.83 | 2.13 | 0.953 | 1.87E−03 |

Overlap between Gene Signatures:

Although the purpose of the two gene signatures developed differ (diagnosis vs staging), an overlap of 8 microRNAs was observed, as shown in FIG. 14. The 8 genes in common to both signatures differ between melanoma patients and normal controls and also have patterns of expression that correlate with disease progression (stage).

Measurement of MEL38 in Melanoma Patient Samples

MicroRNA signature MEL38 was measured in four melanoma patient samples obtained before and 12-14 days after treatment (ie. surgical excision), plus two non-melanoma controls. The value of the MEL38 score and selected individual genes were compared between time points.

Patients and Methods

Plasma from four melanoma patients was collected into EDTA tubes prior to surgical excision (T1) and again 12-14-days later during a follow-up visit (T2) by Cureline Inc (California, USA). Two non-melanoma control samples were also obtained. Specimen and clinical data is shown in Table 15. All biopsies were verified as having clear margins by the referring pathologist (personally comm.). Written informed consent was obtained from each patient.

MicroRNA isolation and Nanostring profiling was performed by Canopy Biosciences (St Louis, MO, USA). Spike-in oligonucleotides corresponding to miR-254 and miR-414 were added to each sample to control for inter-sample variation.

Data analysis was performed also as described above, including negative and positive control adjustment and scaling to housekeeping gene expression. Data processing was performed using nSolver 4.0 (Nanostring Inc, Seattle, USA) and Rstudio (R: A language and environment for statistical computing: R Foundation for Statistical Computing, 2010). The MEL38 gene support vector machine (SVM) classification algorithm was applied to the corresponding genes from each sample and the scores scaled to between 0-10. Individual samples with fewer than 50% of the MEL38 genes detected above background were processed with the Bioconductor rimpute.knn' function with default settings (Gentleman R C, Carey V J, Bates D M, Bolstad B, Dettling M, Dudoit S, et al. Bioconductor: open software development for computational biology and bioinformatics. Genome Biol 2004; 5 (10):R80).

TABLE 15

Melanoma patient and plasma collection information

| Specimen ID | Pathological Diagnosis | Days between excision and follow-up | Age | TNM (T) | TNM (N) | TNM (M) | Stage |
|---|---|---|---|---|---|---|---|
| 7-16155/17 MEL T1 | Malignant melanoma, NOS | 12 | 67 | T1b | N0 | M0 | IB |
| 7-15970/17 MEL T1 | Nodular melanoma | 14 | 83 | T4 | N0 | M0 | IIC |
| 7-16471/17 MEL T1 | Nodular melanoma | 12 | 79 | T4b | N2b | M0 | IIIC |
| 7-17185/17 MEL T1 | Epithelioid cell melanoma | 13 | 84 | pT4b | N3 | MX | IIIC |

Results

Nanostring microRNA profiles from 4 melanoma patients before and after lesion excision and 2 non-melanoma controls were generated, resulting a total of 10 samples. Prior to spike-in gene normalisation, the raw data were visually examined. Spike-in mir-414 exhibited substantially lower and less variable expression than mir-254, suggesting an error in the design of this oligonucleotide or in the laboratory processes. The raw data for mir-254 closely resembled the intensity and inter-sample variation observed in our earlier work, therefore mir-254 alone was used for normalisation in this study.

The MEL38 scores generated from plasma collected at the time of melanoma diagnosis (T1) were significantly higher than the two normal non-melanoma controls, as shown in FIG. 15. The mean MEL38 score for the pre-excision plasma was 8.84, compared to 3.95 for the control samples (T-test P-value <0.001).

The mean MEL38 score of the post-excision (T2) plasma samples was 7.47. A t-test of T2 vs non-melanoma control samples indicated the difference was also statistically significant (P=0.011), although to a lesser extent than the T1 preexcision samples, reflecting the more 'normal-like' status of the T2 samples.

Next, a one-sided paired t-test was performed on the T1 and T2 MEL38 scores from all 4 patients. The mean MEL38 change between patient-matched time points was −15%, which was statistically significant based on a one-sided paired T-test (P=0.030). A general linear model was applied to the T1/T2 data points to test the association of patient age, tumour stage and days between plasma collections with the MEL38 score. None of the variables achieved statistical significance (data not shown) with the T1 vs T2 score being closest at P=0.064. Overall, these data suggest a 'normalisation' of the circulating microRNA profiles of these four patients after surgical excision, as quantified by the MEL38 signature.

Finally, the minimal gene subset required to classify melanoma vs non-melanoma was identified as follows.

Training series; melanoma vs non-melanoma: A melanoma vs non-melanoma classifier was trained using the 17 gene subset of Me138. On the original training series, it achieved 83% cross validation accuracy (83% sensitivity, 81% specificity).

Melanoma T1 vs T2: When the trained 17-gene classification algorithm was applied to clinical dataset data, generated from blood collected before and after melanoma excision, a mean 11% reduction in the Melaseq score was observed between time points. Three patients showed a reduction in their 17-gene classifier scores and 1 patient showed an increase. The paired t-test p-value for this result was 0.065 (approaching significance).

Melanoma vs non-melanoma: Clinical dataset #2 included two non-melanoma control samples also. A comparison between the pre-excision melanoma patient samples (n=5) and the two non-melanoma samples using the 17-gene classifier resulted in a significant result (P=0.020). This shows that the MEL17 subset of MEL38 is able to stratify blood samples based on disease state, despite the reduced number of measurements.

MEL17:

hsa-miR-1258, hsa-miR-1910-5p, hsa-miR-424-5p, hsa-miR-4532, hsa-miR-548a-5p, hsa-miR-181b-5p, hsa-miR-34a-5p, hsa-miR-497-5p, hsa-miR-152-3p, hsa-miR-299-3p, hsa-miR-454-3p, hsa-miR-1302, hsa-miR-219a-2-3p, hsa-miR-548ad-3p, hsa-miR-1264, hsa-miR-154-5p and hsa-miR-431-5p.

Conclusion

In the four patients analysed in this study, a mean reduction of the MEL38 score of 15% and MEL17 score of 11% was observed between diagnosis and a 12-14-day follow-up visit. The differences in MEL38 between T1 and T2 time points were significantly different and each time point was significantly different to normal non-melanoma control samples. These observations suggest that at 12-14 days post excision, the circulating microRNA profile of a melanoma patient with a completely excised tumour has been altered, becoming more 'normal-like' after melanoma excision.

Referring to FIG. 16, a block diagram illustrating a system 1000 embodying the present invention. A public communications network 1002, such as the Internet, is employed for messaging between a secure server 1004 and endpoint devices 1006. Generally speaking, the user endpoint devices 1006 may be any suitable computing, communications and/or processing appliances having the ability to communicate via the Internet 1002, for example using web browser software and/or other connected applications. Furthermore, while the exemplary system 1000 comprises a single shared, insecure, network 1002 for communications between all processing devices and systems, embodiments of the invention may include other types of communications and/or transaction networks, such as financial transaction networks, private networks, virtual private networks (VPNs), cellular telephony networks, or a mix of these and/or other forms of communications systems.

It will therefore be understood that where the term 'network interface' is used throughout this specification, unless otherwise required by the context, it refers to a combination of physical hardware and/or network interface software (protocol stack) implementing the various communications protocols required to exchange information with other devices via one or more corresponding physical or virtual communications networks.

As illustrated in the system 1000, the secure server 1004 is able to communicate via the public network 1002. The secure server 1004 comprises a processor 1328, which is interfaced to, or otherwise operably associated with, a further non-volatile memory/storage device 1330. The processor 1328 is also interfaced to volatile storage 1332, which contains program instructions and transient data relating to the operation of the secure server 1004.

The processor 1328 is operably associated with a communications interface 1334, via which it is able to communicate over the public network 1002 with the endpoint devices 1006.

In use, the volatile storage 1332 includes a corresponding body 1336 of program instructions configured to perform processing and operations embodying features of the present invention, comprising various functional elements of the system 1000 as described below. The secure server 1004 is also connected to a telecommunications service provider network 1338, such as the public switched telephony network (PSTN) via a network termination unit (NTU) 1340. This enables the secure server 1004 to engage in communications with end-users via the PSTN 1338. Such communications may comprise voice telephony calls, automated telephony calls, and SMS messaging. In the exemplary system 1000, the PSTN 1338 is shown connected to a cellular mobile base station 1342, facilitating communications with a mobile device 1007 of an end-user who is also accessing the secure server 1004 via an endpoint device 1006.

In this specification, terms such as 'processor', 'computer', and so forth, unless otherwise required by the context, should be understood as referring to a range of possible implementations of devices, apparatus and systems comprising a combination of hardware and software. This includes single-processor and multi-processor devices and apparatus, including portable devices, desktop computers, and various types of server systems, including cooperating hardware and software platforms that may be co-located or distributed. Hardware may include conventional personal computer architectures, or other general-purpose hardware platforms. Software may include commercially available operating system software in combination with various application and service programs. Alternatively, computing or processing platforms may comprise custom hardware and/or software architectures. For enhanced scalability, computing and processing systems may comprise cloud computing platforms, enabling physical hardware resources to be allocated dynamically in response to service demands. While all of these variations fall within the scope of the present invention, for ease of explanation and understanding the exemplary embodiments described herein are based upon single-processor general-purpose computing platforms, commonly available operating system platforms, and/or widely available consumer products, such as desktop PCs, notebook or laptop PCs, smartphones, tablet computers, and so forth.

In particular, the term 'processing unit' is used in this specification (including the claims) to refer to any suitable combination of hardware and software configured to perform a particular defined task, such as generating and transmitting data, receiving and processing data, or receiving and validating data. Such a processing unit may comprise an executable code module executing at a single location on a single processing device, or may comprise cooperating executable code modules executing in multiple locations and/or on multiple processing devices. For example, in some embodiments of the invention processing may be performed entirely by code executing on secure server 1004, while in other embodiments corresponding processing may be performed cooperatively by code modules executing on endpoint devices 1006. For example, embodiments of the invention may employ application programming interface (API) code modules, installed at the secure server 1004, or at another third-party system, configured to operate cooperatively with code modules executing on endpoint devices 1006 in order to provide the secure server 1004 with functionality.

Software components embodying features of the invention may be developed using any suitable programming language, development environment, or combinations of languages and development environments, as will be familiar to persons skilled in the art of software engineering. For example, suitable software may be developed using the C programming language, the Java programming language, the C++ programming language, the Go programming language, and/or a range of languages suitable for implementation of network or web-based services, such as JavaScript, HTML, PHP, ASP, JSP, Ruby, Python, and so forth. These examples are not intended to be limiting, and it will be appreciated that convenient languages or development systems may be employed, in accordance with system requirements.

In the exemplary system 1000, the endpoint devices 1006 each comprise a processor. The processor is interfaced to, or otherwise operably associated with, a communications interface, one or more user input/output (I/O) interfaces, and local storage, which may comprise a combination of volatile and non-volatile storage. Non-volatile storage may include solid-state non-volatile memory, such as read only memory (ROM) flash memory, or the like. Volatile storage may include random access memory (RAM). The storage contains program instructions and transient data relating to the operation of the endpoint device 1006. In some embodiments, the endpoint device 1006 may include additional peripheral interfaces, such as an interface to high-capacity non-volatile storage, such as a hard disk drive, optical drive, and so forth (not shown in FIG. 16).

The endpoint device storage may contain program and data content relevant to the normal operation of the device. This may include operating system programs and data (e.g. associated with a Windows, Android, iOS, MacOS or Unix-based operating system), as well as other executable application software generally unrelated to the present invention. The storage also includes program instructions which, when executed by the processor instruct the endpoint device 1006 to perform operations relating to an embodiment of the invention, for example such as are described below.

As also shown in FIG. 16, the secure server 1004 comprises a processor 1328. The processor 1328 is interfaced to, or otherwise operably associated with a non-volatile memory/storage device 1330, which may be a hard disk drive, and/or may include a solid-state non-volatile memory, such as ROM, flash memory, or the like. The processor 1328 is also interfaced to volatile storage 1332, such as RAM, which contains program instructions and transient data relating to the operation of the secure server 1004.

In a conventional configuration, the storage device 1330 maintains known program and data content relevant to the normal operation of the endpoint devices 1006. For example, the storage device 1330 may contain operating system programs and data, as well as other executable application software necessary for the intended functions of endpoint devices 1006. The storage device 1330 also contains program instructions which, when executed by the processor 1328, instruct the endpoint devices 1006 to perform operations relating to an embodiment of the present invention, such as are described in greater detail below. In operation, instructions and data held on the storage device 1330 are transferred to volatile memory 1332 for execution on demand.

The processor 1328 is also operably associated with a communications interface 1334 in a conventional manner. The communications interface 1334 facilitates access to the data communications network 1002.

In use, the volatile storage 1332 contains a corresponding body 1336 of program instructions transferred from the storage device 1330 and configured to perform processing and other operations embodying features of the present invention.

The secure server 1004 permits user access to data obtained by a clinician corresponding to a biological sample stored in storage device 1330 or on cloud storage such as Amazon Web Services or Microsoft Azure or other content delivery network (CDN) or on local storage of endpoint device 1006. The collected data from the sample is stored in a data file or as a data record in a database accessible by the secure server 1004 or endpoint devices 1006. The data file may be copied or uploaded to a computer 110 and stored on a local storage device.

The trained machine learning model(s) (for example, in the form of a model file) may be stored on storage device 1330 of secure server 1004 or local storage of endpoint devices 1006. The processor 1328 or processor of endpoint devices 1006 will execute program instructions via a machine learning engine supplied with new unseen biological sample data to perform the machine learning inference. For inferencing, data corresponding to a biological sample is classified according to the trained machine learning model(s) as described earlier. The classification can be recorded with the data record in the database or a separate file associated with the data file.

The invention claimed is:

1. A method comprising administering an anti-cancer agent to an individual diagnosed with melanoma, wherein the diagnosis is based on determining or having determined a difference in miRNA expression signature in the individual relative to an miRNA expression signature in one or more individuals without melanoma, wherein the miRNA expression signature consists of expression of miRNAs:

hsa-miR-1258 (SEQ ID-NO: 4),
hsa-miR-1264 (SEQ ID-NO: 5),
hsa-miR-1269a (SEQ ID-NO: 6), -continued hsa-miR-1302 (SEQ ID-NO: 8),
hsa-miR-1306-5p (SEQ ID-NO: 9),
hsa-miR-138-5p (SEQ ID-NO: 10),
hsa-miR-152-3p (SEQ ID-NO: 11),
hsa-miR-1537-3p (SEQ ID-NO: 12),
hsa-miR-154-5p (SEQ ID-NO: 13),
hsa-miR-1-5p (SEQ ID-NO: 14),
hsa-miR-181b-5p (SEQ ID-NO: 15),
hsa-miR-1910-5p (SEQ ID-NO: 16),
hsa-miR-1973 (SEQ ID-NO: 17),
hsa-miR-205-5p (SEQ ID-NO: 19),
hsa-miR-219a-2-3p (SEQ ID-NO: 20),
hsa-miR-2682-5p (SEQ ID NO: 21),
hsa-miR-27a-3p (SEQ ID-NO: 22),
hsa-miR-299-3p (SEQ ID NO: 23,
hsa-miR-301a-3p (SEQ ID-NO: 24),
hsa-miR-3131 (SEQ ID-NO: 26),
hsa-miR-337-5p (SEQ ID-NO: 28),
hsa-miR-34a-5p (SEQ ID-NO: 29),
hsa-miR-3928-3p (SEQ ID-NO: 30),
hsa-miR-424-5p (SEQ ID-NO: 31),
hsa-miR-431-5p (SEQ ID NO: 32),
hsa-miR-450a-5p (SEQ ID-NO: 33),
hsa-miR-4532 (SEQ ID NO: 34),
hsa-miR-454-3p (SEQ ID-NO: 35),
hsa-miR-4787-3p (SEQ ID-NO: 36,
hsa-miR-497-5p (SEQ ID-NO: 37),
hsa-miR-520d-3p (SEQ ID-NO: 38),
hsa-miR-522-3p (SEQ ID-NO: 40),
hsa-miR-548a-5p (SEQ ID-NO: 41),
hsa-miR-548ad-3p (SEQ ID-NO: 42),
hsa-miR-5481 (SEQ ID-NO: 43).

-continued hsa-miR-553 (SEQ ID-NO: 44),
hsa-miR-624-3p (SEQ ID-NO: 45), and
hsa-miR-764 (SEQ ID NO: 48);

wherein the difference in the miRNA expression signature is determined from a plasma sample or a melanoma tissue sample from the individual and is relative to an miRNA expression signature determined from the one or more individuals without melanoma for each of said miRNAs;

and wherein the anti-cancer agent comprises interleukin-2, recombinant interferon-alpha 2b ipilimumab, nivolumab, pembrolizumab, cobimetinib, trametinib, dabrafenib or vemurafenib.

2. The method of claim 1, wherein the ipilimumab, or the nivolumab, or the pembrolizumab is administered.

3. The method of claim 1, wherein the cobimetinib or the trametinib is administered.

4. The method of claim 1, wherein the dabrafenib or the vemurafenib is administered.

5. The method of claim 1, wherein the sample from which the difference in the miRNA expression signature is determined comprises the plasma.

6. The method of claim 1, wherein the sample from which the difference in the miRNA expression signature is determined comprises the melanoma tissue.

* * * * *

SEQUENCE LISTING

```
Sequence total quantity: 48
SEQ ID NO: 1              moltype = RNA   length = 22
FEATURE                   Location/Qualifiers
source                    1..22
                          mol_type = other RNA
                          organism = Homo sapiens
SEQUENCE: 1
tgaggtagga ggttgtatag tt                                                   22

SEQ ID NO: 2              moltype = RNA   length = 23
FEATURE                   Location/Qualifiers
source                    1..23
                          mol_type = other RNA
                          organism = Homo sapiens
SEQUENCE: 2
tcaaatgctc agactcctgt ggt                                                  23

SEQ ID NO: 3              moltype = RNA   length = 22
FEATURE                   Location/Qualifiers
source                    1..22
                          mol_type = other RNA
                          organism = Homo sapiens
SEQUENCE: 3
tttccggctc gcgtgggtgt gt                                                   22

SEQ ID NO: 4              moltype = RNA   length = 21
FEATURE                   Location/Qualifiers
source                    1..21
                          mol_type = other RNA
                          organism = Homo sapiens
SEQUENCE: 4
agttaggatt aggtcgtgga a                                                    21

SEQ ID NO: 5              moltype = RNA   length = 23
FEATURE                   Location/Qualifiers
source                    1..23
                          mol_type = other RNA
                          organism = Homo sapiens
SEQUENCE: 5
caagtcttat ttgagcacct gtt                                                  23

SEQ ID NO: 6              moltype = RNA   length = 22
FEATURE                   Location/Qualifiers
source                    1..22
                          mol_type = other RNA
                          organism = Homo sapiens
SEQUENCE: 6
ctggactgag ccgtgctact gg                                                   22

SEQ ID NO: 7              moltype = RNA   length = 22
FEATURE                   Location/Qualifiers
source                    1..22
                          mol_type = other RNA
                          organism = Homo sapiens
SEQUENCE: 7
ctgaagctca gagggctctg at                                                   22

SEQ ID NO: 8              moltype = RNA   length = 21
FEATURE                   Location/Qualifiers
source                    1..21
                          mol_type = other RNA
                          organism = Homo sapiens
SEQUENCE: 8
ttgggacata cttatgctaa a                                                    21

SEQ ID NO: 9              moltype = RNA   length = 22
FEATURE                   Location/Qualifiers
source                    1..22
                          mol_type = other RNA
                          organism = Homo sapiens
SEQUENCE: 9
ccacctcccc tgcaaacgtc ca                                                   22

SEQ ID NO: 10             moltype = RNA   length = 23
FEATURE                   Location/Qualifiers
source                    1..23
                          mol_type = other RNA
                          organism = Homo sapiens
```

```
SEQUENCE: 10
agctggtgtt gtgaatcagg ccg                                          23

SEQ ID NO: 11           moltype = RNA   length = 21
FEATURE                 Location/Qualifiers
source                  1..21
                        mol_type = other RNA
                        organism = Homo sapiens
SEQUENCE: 11
tcagtgcatg acagaacttg g                                            21

SEQ ID NO: 12           moltype = RNA   length = 22
FEATURE                 Location/Qualifiers
source                  1..22
                        mol_type = other RNA
                        organism = Homo sapiens
SEQUENCE: 12
aaaaccgtct agttacagtt gt                                           22

SEQ ID NO: 13           moltype = RNA   length = 22
FEATURE                 Location/Qualifiers
source                  1..22
                        mol_type = other RNA
                        organism = Homo sapiens
SEQUENCE: 13
taggttatcc gtgttgcctt cg                                           22

SEQ ID NO: 14           moltype = RNA   length = 22
FEATURE                 Location/Qualifiers
source                  1..22
                        mol_type = other RNA
                        organism = Homo sapiens
SEQUENCE: 14
acatacttct ttatatgccc at                                           22

SEQ ID NO: 15           moltype = RNA   length = 23
FEATURE                 Location/Qualifiers
source                  1..23
                        mol_type = other RNA
                        organism = Homo sapiens
SEQUENCE: 15
aacattcatt gctgtcggtg ggt                                          23

SEQ ID NO: 16           moltype = RNA   length = 21
FEATURE                 Location/Qualifiers
source                  1..21
                        mol_type = other RNA
                        organism = Homo sapiens
SEQUENCE: 16
ccagtcctgt gcctgccgcc t                                            21

SEQ ID NO: 17           moltype = RNA   length = 19
FEATURE                 Location/Qualifiers
source                  1..19
                        mol_type = other RNA
                        organism = Homo sapiens
SEQUENCE: 17
accgtgcaaa ggtagcata                                               19

SEQ ID NO: 18           moltype = RNA   length = 23
FEATURE                 Location/Qualifiers
source                  1..23
                        mol_type = other RNA
                        organism = Homo sapiens
SEQUENCE: 18
cccagtgttt agactatctg ttc                                          23

SEQ ID NO: 19           moltype = RNA   length = 22
FEATURE                 Location/Qualifiers
source                  1..22
                        mol_type = other RNA
                        organism = Homo sapiens
SEQUENCE: 19
tccttcattc caccggagtc tg                                           22

SEQ ID NO: 20           moltype = RNA   length = 22
FEATURE                 Location/Qualifiers
source                  1..22
                        mol_type = other RNA
```

```
                       organism = Homo sapiens
SEQUENCE: 20
agaattgtgg ctggacatct gt                                              22

SEQ ID NO: 21          moltype = RNA  length = 23
FEATURE                Location/Qualifiers
source                 1..23
                       mol_type = other RNA
                       organism = Homo sapiens
SEQUENCE: 21
caggcagtga ctgttcagac gtc                                             23

SEQ ID NO: 22          moltype = RNA  length = 21
FEATURE                Location/Qualifiers
source                 1..21
                       mol_type = other RNA
                       organism = Homo sapiens
SEQUENCE: 22
ttcacagtgg ctaagttccg c                                               21

SEQ ID NO: 23          moltype = RNA  length = 22
FEATURE                Location/Qualifiers
source                 1..22
                       mol_type = other RNA
                       organism = Homo sapiens
SEQUENCE: 23
tatgtgggat ggtaaaccgc tt                                              22

SEQ ID NO: 24          moltype = RNA  length = 23
FEATURE                Location/Qualifiers
source                 1..23
                       mol_type = other RNA
                       organism = Homo sapiens
SEQUENCE: 24
cagtgcaata gtattgtcaa agc                                             23

SEQ ID NO: 25          moltype = RNA  length = 23
FEATURE                Location/Qualifiers
source                 1..23
                       mol_type = other RNA
                       organism = Homo sapiens
SEQUENCE: 25
atcagggctt gtggaatggg aag                                             23

SEQ ID NO: 26          moltype = RNA  length = 23
FEATURE                Location/Qualifiers
source                 1..23
                       mol_type = other RNA
                       organism = Homo sapiens
SEQUENCE: 26
tcgaggactg gtggaagggc ctt                                             23

SEQ ID NO: 27          moltype = RNA  length = 21
FEATURE                Location/Qualifiers
source                 1..21
                       mol_type = other RNA
                       organism = Homo sapiens
SEQUENCE: 27
gcccctgggc ctatcctaga a                                               21

SEQ ID NO: 28          moltype = RNA  length = 21
FEATURE                Location/Qualifiers
source                 1..21
                       mol_type = other RNA
                       organism = Homo sapiens
SEQUENCE: 28
gaacggcttc atacaggagt t                                               21

SEQ ID NO: 29          moltype = RNA  length = 22
FEATURE                Location/Qualifiers
source                 1..22
                       mol_type = other RNA
                       organism = Homo sapiens
SEQUENCE: 29
tggcagtgtc ttagctggtt gt                                              22

SEQ ID NO: 30          moltype = RNA  length = 22
FEATURE                Location/Qualifiers
source                 1..22
```

-continued

```
                        mol_type = other RNA
                        organism = Homo sapiens
SEQUENCE: 30
ggaggaacct tggagcttcg gc                                            22

SEQ ID NO: 31           moltype = RNA   length = 22
FEATURE                 Location/Qualifiers
source                  1..22
                        mol_type = other RNA
                        organism = Homo sapiens
SEQUENCE: 31
cagcagcaat tcatgttttg aa                                            22

SEQ ID NO: 32           moltype = RNA   length = 21
FEATURE                 Location/Qualifiers
source                  1..21
                        mol_type = other RNA
                        organism = Homo sapiens
SEQUENCE: 32
tgtcttgcag gccgtcatgc a                                             21

SEQ ID NO: 33           moltype = RNA   length = 22
FEATURE                 Location/Qualifiers
source                  1..22
                        mol_type = other RNA
                        organism = Homo sapiens
SEQUENCE: 33
ttttgcgatg tgttcctaat at                                            22

SEQ ID NO: 34           moltype = RNA   length = 17
FEATURE                 Location/Qualifiers
source                  1..17
                        mol_type = other RNA
                        organism = Homo sapiens
SEQUENCE: 34
ccccggggag cccggcg                                                  17

SEQ ID NO: 35           moltype = RNA   length = 23
FEATURE                 Location/Qualifiers
source                  1..23
                        mol_type = other RNA
                        organism = Homo sapiens
SEQUENCE: 35
tagtgcaata ttgcttatag ggt                                           23

SEQ ID NO: 36           moltype = RNA   length = 24
FEATURE                 Location/Qualifiers
source                  1..24
                        mol_type = other RNA
                        organism = Homo sapiens
SEQUENCE: 36
gatgcgccgc ccactgcccc gcgc                                          24

SEQ ID NO: 37           moltype = RNA   length = 21
FEATURE                 Location/Qualifiers
source                  1..21
                        mol_type = other RNA
                        organism = Homo sapiens
SEQUENCE: 37
cagcagcaca ctgtggtttg t                                             21

SEQ ID NO: 38           moltype = RNA   length = 22
FEATURE                 Location/Qualifiers
source                  1..22
                        mol_type = other RNA
                        organism = Homo sapiens
SEQUENCE: 38
aaagtgcttc tctttggtgg gt                                            22

SEQ ID NO: 39           moltype = RNA   length = 22
FEATURE                 Location/Qualifiers
source                  1..22
                        mol_type = other RNA
                        organism = Homo sapiens
SEQUENCE: 39
aacgcacttc cctttagagt gt                                            22

SEQ ID NO: 40           moltype = RNA   length = 22
FEATURE                 Location/Qualifiers
```

```
SEQ ID NO: 40
source          1..22
                mol_type = other RNA
                organism = Homo sapiens
SEQUENCE: 40
aaaatggttc cctttagagt gt                                              22

SEQ ID NO: 41          moltype = RNA   length = 22
FEATURE                Location/Qualifiers
source                 1..22
                       mol_type = other RNA
                       organism = Homo sapiens
SEQUENCE: 41
aaaagtaatt gcgagtttta cc                                              22

SEQ ID NO: 42          moltype = RNA   length = 22
FEATURE                Location/Qualifiers
source                 1..22
                       mol_type = other RNA
                       organism = Homo sapiens
SEQUENCE: 42
gaaaacgaca atgacttttg ca                                              22

SEQ ID NO: 43          moltype = RNA   length = 22
FEATURE                Location/Qualifiers
source                 1..22
                       mol_type = other RNA
                       organism = Homo sapiens
SEQUENCE: 43
aaaagtattt gcgggttttg tc                                              22

SEQ ID NO: 44          moltype = RNA   length = 21
FEATURE                Location/Qualifiers
source                 1..21
                       mol_type = other RNA
                       organism = Homo sapiens
SEQUENCE: 44
aaaacggtga gattttgttt t                                               21

SEQ ID NO: 45          moltype = RNA   length = 21
FEATURE                Location/Qualifiers
source                 1..21
                       mol_type = other RNA
                       organism = Homo sapiens
SEQUENCE: 45
cacaaggtat tggtattacc t                                               21

SEQ ID NO: 46          moltype = RNA   length = 21
FEATURE                Location/Qualifiers
source                 1..21
                       mol_type = other RNA
                       organism = Homo sapiens
SEQUENCE: 46
aatggcgcca ctagggttgt g                                               21

SEQ ID NO: 47          moltype = RNA   length = 22
FEATURE                Location/Qualifiers
source                 1..22
                       mol_type = other RNA
                       organism = Homo sapiens
SEQUENCE: 47
tacccattgc atatcggagt tg                                              22

SEQ ID NO: 48          moltype = RNA   length = 22
FEATURE                Location/Qualifiers
source                 1..22
                       mol_type = other RNA
                       organism = Homo sapiens
SEQUENCE: 48
gcaggtgctc acttgtcctc ct                                              22
```